US005693607A

United States Patent [19]
Segarini et al.

[11] Patent Number: 5,693,607
[45] Date of Patent: Dec. 2, 1997

[54] USES OF TGF-β RECEPTOR FRAGMENT AS A THERAPEUTIC AGENT

[76] Inventors: Patricia R. Segarini, 38 Devonshire Ave., #5, Mountain View, Calif. 94043; James R. Dasch, 837 Seminole, Redwood City, Calif. 94062; David R. Olsen, 276 Hedge Rd., Menlo Park, Calif. 94025; Pedro A. Carrillo, 1966 California St., #7, San Francisco, Calif. 94109; Desmond Mascarenhas, 1074 Morningside Dr., Sunnyvale, Calif. 94087

[21] Appl. No.: 361,873

[22] Filed: Dec. 22, 1994

Related U.S. Application Data

[63] Continuation of Ser. No. 37,597, Mar. 26, 1993, abandoned, which is a continuation-in-part of Ser. No. 968,375, Oct. 29, 1992, abandoned.

[51] Int. Cl.$^6$ .......................... C12N 15/12; A61K 38/17
[52] U.S. Cl. .................................. 514/2; 514/8; 435/69.1
[58] Field of Search ........................... 514/2, 8; 435/69.1

[56] References Cited

U.S. PATENT DOCUMENTS

| | | |
|---|---|---|
| 4,886,747 | 12/1989 | Dernyck et al. . |
| 5,084,384 | 1/1992 | Wong et al. . |
| 5,187,151 | 2/1993 | Clark et al. . |

FOREIGN PATENT DOCUMENTS

| | | |
|---|---|---|
| 0 369 861 A2 | 5/1990 | European Pat. Off. . |
| 0413440 | 2/1991 | European Pat. Off. . |
| 0637450 | 2/1995 | European Pat. Off. . |
| WO 88/02406 | 4/1988 | WIPO . |
| WO 89/12678 | 12/1989 | WIPO . |
| WO 91/19513 | 12/1991 | WIPO . |
| WO 92/17206 | 10/1992 | WIPO . |
| WO 93/09228 | 5/1993 | WIPO . |
| WO 93/10215 | 5/1993 | WIPO . |
| WO 93/17708 | 9/1993 | WIPO . |
| WO 94/18991 | 9/1994 | WIPO . |
| WO95/10610 | 4/1995 | WIPO . |

OTHER PUBLICATIONS

Roberts, A.B., et al., "Chapter 8: The Transforming Growth Factor–βs", in *Handbook Exp. Pharm., Peptide Growth Factors and Their Receptors I*, Sporn, M.B., et al., editors, (published by Springer–Verlag, New York, 1990), vol. 95, pp. 419–458.

Wahl, S.M., et al., "Inflammatory and Immunomodulatory Roles of TGF–β", *Immunology Today* (1989) 10(8):258–261.

Kim, S–J., et al, "Autoinduction of Transforming Growth Factor β1 Is Mediated By the AP–1 Complex", *Mol. Cell. Biol.* (1990) 10(4):1492–1497.

Mauer, S.M., et al., "Structural–Functional Relationships in Diabetic Nephropathy", *J. Clin. Invest.* (1984) 74:1143–1155.

Canney, P.A., et al., "Transforming Growth Factor Beta: A Promoter of Late Connective Tissue Injury Following Radiotherapy", *British J. Radiol.* (1990) 63:620–623.

Border, W.A., et al., "Suppression of Experimental Glomerulonephritis by Antiserum Against Transforming Growth Factor β1", *Nature* (1990) 346:371–374.

Border, W.A., et al., "Antagonists of Transforming Growth Factor–β: A Novel Approach to Treatment of Glomerulonephritis and Prevention of Glomerulosclerosis", *Kidney Int.* (1992) 41:566–570.

Wahl, S.M., et al., "Reversal of Acute and Chronic Synovial Inflammation by Anti–Transforming Growth Factor Beta", *J. Exp. Med.* (1993) 177(1):225–230.

Wahl, S.M, "Transforming Growth Factor Beta (TGF–β) in Inflammation: A Cause and a Cure", *J. Clin. Immunol.* (1992) 12(2):1–14.

Goddard, D.H., et al., "Autocrine Regulation of Rheumatoid Arthritis Synovial Cell Growth in Vitro", *Cytokine* (1990) 2:149–155.

Shah, M., et al., "Control of Scarring in Adult Wounds by Neutralizing Antibody to Transforming Growth Factor β", *The Lancet* (1992) 339:213–214.

Kekow, J., et al., "Transforming Growth Factor β and Noncytopathic Mechanisms of Immunodeficiency in Human Immunodeficiency Virus Infection", *Proc. Natl. Acad. Sci. USA* (1990) 87:8321–8325.

Steiner, M.S., "Transforming Growth Factor–β1 Overproduction in Prostate Cancer: Effects on Growth in Vivo and in Vitro", *Mol. Endocrinol.* (1992) 6:15–25.

Merz, V.W., et al., "Elevated Transforming Growth Factor–β1 and β3 mRNA Levels are Assoicated with ras+ myc–Induced Carcinomas in Reconstituted Mouse Prostate: Evidence for a Paracrine Role During Progression", *Mol. Endocrinal.* (1991) 5:503–513.

Okuda, S., et al., "Dietary Protein Restriction Rapidly Reduces Transforming Growth Factor β1 Expression in Experimental Glomerulonephritis", *Proc. Natl. Acad. Sci. U.S.A.* (1991) 88:9765–9769.

Yamaguchi, Y., et al., "Negative Regulation of Transforming Growth Factor–β By The Proteoglycan Decorin", *Nature* (1990) 346:281–284.

Andres, J.L., et al., "Membrane–Anchored and Soluble Forms of Betaglycan, a Polymorphic Proteoglycan That Binds Transforming Growth Factor–β", *J. Cell Biol.* (1989) 109:3137–3145.

Lin, H.Y., et al., "Expression Cloning the TGF–β Type II Receptor, A Functional Transmembrane Serine/Threonine Kinase", *Cell* (1992) 68:775–785.

Ecker, D.J., et al., "Increasing Gene Expression in Yeast by Fusion to Ubiquitin", *J. Biol. Chem.* (1989) 264(13):7715–7719.

(List continued on next page.)

*Primary Examiner*—David L. Fitzgerald
*Attorney, Agent, or Firm*—Morrison & Foerster

[57] ABSTRACT

A method of treating TGF–β excess is disclosed. The treatment is parenteral, oral or topical administration of TGF–β receptor fragment. Particularly effective is a soluble receptor fragment which resembles the extracellular portion of TGF–β binding protein II.

5 Claims, 2 Drawing Sheets

OTHER PUBLICATIONS

Standaert. R.F., et al., "Molecular Cloning and Overexpression of the Human FK506–Binding Protein FKBP", *Nature* (1990) 346:671–674.

Koltin, Y., et al., "Rapamycin Sensitivity in *Saccharomyces cerevisiae* Is Mediated by a Peptidyl–Prolyl cis–trans Isomerase Related to Human FK506–Binding Protein", *Mol. Cell. Biol.* (1991) 11(3):1718–1723.

Gasser, C.S., et al., "Structure and Expression of Cytosolic Cyclophilin/Peptidyl–Prolyl Cis–Trans Isomerase of Higher Plants and Production of Active Tomato Cyclophilin in *Escherichia coli*", *Proc. Natl. Acad. Sci. USA* (1990) 87:9519–9523.

Holtzman, T.F., et al., "Preliminary Characterization of a Cloned Neutral Isoelectric Form of the Human Peptidyl Prolyl Isomerase Cyclophilin", *J. Biol. Chem.* (1991) 266(4):2474–2479.

Liu, J., et al., "Cloning, Expression, and Purification of Human Cyclophilin in *Escherichia coli* and Assessment of the Catalytic Role of Cysteines by Site–Directed Mutagenesis", *Proc. Natl. Acad. Sci. USA* (1990) 87:2304–2308.

Liu, J., et al., "Peptidyl–Prolyl Cis–Trans–Isomerase From *Escherichia coli*: A Periplasmic Homolog of Cyclophilin That Is Not Inhibited By Cyclosporin A", *Proc. Natl. Acad. Sci. USA* (1990) 87:4028–4032.

Allen, J. B., "Rapid Onset Synovial Inflammation Hyperplasia Induced by Transforming Growth Factor β", *J. Exp. Med.* (1990) 171:231–247.

Armendariz–Borunda, J., et al., "Regulation of TGFβ Gene Expression in Rat Liver Intoxicated with Carbon Tetrachloride", *The FASEB Journal* (1990) 4:215–220.

Berg, D.J., "Immune Dysfunction in Mice With Plasmacytomas. I. Evidence That Transforming Growth Factor–β Contributes to the Altered Expression of Activation Receptors on Host B Lymphocytes", *J. Immunology* (1991) 146(8):2865–2872.

Bodmer, S., et al. "Immunosuppression and Transforming Growth Factor–β in Glioblastoma", *J. Immunology* (1989):143(10) 3222–3229.

Border, W.A., et al., "Transforming Growth Factor–β in Disease: The Dark Side of Tissue Repair", *J. Clin. Invest.* (1992) 90:1–7.

Broekelmann, T.J., "Transforming Growth Factor β1 is Present at Sites of Extracellular Matrix Gene Expression in Human Pulmonary Fibrosis", *Proc. Natl. Acad. Sci.* (1991) 88:6642–6646.

Castilla, A., "Transforming Growth Factors β1 and α in Chronic Liver Disease: Effects of Interferon Alfa Therapy", *New England Journal of Medicine* (1991) 324(14):933–940.

Coimbra, T., et al., "Transforming Growth Factor–β Productions in Anti–Glomerular Basement Membrane Disease in the Rabbit", *Am. J. Pathology* (1991) 138(1):223–234.

Connor, T.B., et al., "Correlation of Fibrosis and Transforming Growth Factor–β Type 2 Levels in the Eye", *J. Clin. Invest.* (1989) 83:1661–1666.

Czaja, M.J., "In Vitro and In Vivo Association of Transforming Growth Factor–β1 with Hepatic Fibrosis", *J. Cell Biology* (1989) 108(6) 2477–2482.

Dasch, J.R., et al., "Capture Immunoassays Specific for TGFβ1 and TGFβ2: Use in Pharmacokinetic Studies", *Annals of the New York Academy of Sciences* (1990) vol. 593, pp. 303–305.

Deguchi, Y., "Spontaneous Increase of Transforming Growth Factor β Production by Bronchoalveolar Mononuclear Cells of Patients with Systemic Autoimmune Diseases Affected the Lung", *Annals of the Rheumatic Diseases* (1991) 51:362–365.

Fava, R., et al., "Active and Latent Forms of Transforminng Growth Factor β Activity in Synovial Effusions", *J. Exp. Med.* (1989) 169:291–296.

Glaser, B.M., et al., "Transforming Growth Factor–β2 for the Treatment of Full–Thickness Macular Holes: A Prospective Randomized Study", *Ophthalmology* (1992) 99(7)1162–173.

Khalil, N., et al., "Increased Production and Immunohistochemical Localization of Transforming Growth Factor–β in Idiopathic Pulmonary Fibrosis", *Am. J. Respir. Cell Mol. Biol.* (1991) 5:155–162.

Khalil, N., et al., "Macrophage Production of Transforming Growth Factor β and Fibroblast Collagen Systhesis in Chronic Pulmonary Inflammation", *J. Exp. Med.* (1989) 170:727–737.

Kim, S–J., et al., "Overexpression of Transforming Growth Factor–β in Transgenic Mice Carrying the Human T–Cell Lymphotropic Virus Type I tax Gene", *Mole. Cell. Biol.* (1991) 11(10):5222–5228.

Kulozik, M., et al., "Co–Localization of Transforming Growth Factor β2 with α1(I) Procollagen mRNA in Tissue Sections of Patients with Systemic Sclerosis", *J. Clin. Invest.* (1990)86:917–922.

Kunkel, T.A., "Rapid and Efficient Site–Specific Mutagenesis Without Phenotypic Selection", *Proc. Natl. Acad. Sci.* (1985) 82:488–492.

Lazdins, J.K., et al., "TGF–β: Upregulator of HIV Replication in Macrophages", *Res. Virol.* (1991) 142:239–242.

Lindholm, D., et al., "Transforming Growth Factor–β1 in the Rat Brain: Increase After Injury and Inhibition of Astrocyte Proliferation", *J. Cell Biology* (1992) 117(2):395–400.

Lotz, M., et al., "Transforming Growth Factor–β and Cellular Immune Responses in Synovial Fluids", *J. Immunology* (1990) 144(11):4189–4194.

Milani, S., et al., "Transforming Growth Factors β1 and β2 Are Differently Expressed in Fibrotic Liver Disease", *Am. J. Pathology* (1991) 139(6):1221–1229.

Ohno, I., et al., "Eosinophils in Chronically Inflamed Human Upper Airway Tissues Express Transforming Growth Factor β1 Gene (TGFβ1)", *J. Clin. Invest.* (1992) 89:1662–1668.

Peltonen, J., et al., "Evaluation of Transforming Growth Factor β and Type I Procollagen Gene Expression in Fibrotic Skin Diseases by In Situ Hybridization", *J. Invest. Dermatology* (1990) 94(3):365–371.

Seed, B., et al., "Molecular Cloning of the CD2 Antigen, the T–Cell Erythrocyte Receptor, by a Rapid Immunoselection Procedure", *Proc. Natl. Acad. Sci. USA* (1987) 84:3365–3369.

Segarini, P.R., et al., "Binding of Transforming Growth Factor–β to Cell Surface Proteins Varies with Cell Type", *Molecular Endocrinology* (1989) 3(2):261–272.

Sporn, M.B., et al., "Autocrine Secretion—10 Years Later", *Annals of Internal Medicine* (1992) 117(5):408–414.

Su, H.C., et al., "A Role for Transforming Growth Factor–β1 in Regulating Natural Killer Cell and T Lymphocyte Proliferative Responses During Acute Infection With Lymphocytic Choriomeningitis Virus", *J. Immunol.* (1991) 147(8):2717–2727.

Towbin, H., et al., "Electrophoretic Transfer of Proteins from Polyacrylamide Gels to Nitrocellulose Sheets: Procedure and Some Applications", *Proc. Natl. Acad. Sci. USA* (1979) 76(9):4350–4354.

Wahl, S.M., et al., "Antagonistic and Agonistic Effects of Transforming Growth Factor-β and IL-1 in Rheumatoid Synovium", *J. Immunology* (1990) 145(8):2514–2519.

Williams, R.S., et al., "Effect of Transforming Growth Factor β on Postoperative Adhesion Formation and Intact Peritoneum", *J. Surg. Research* (1992) 52:65–70.

Wrann, M., et al., "T. Cell Suppressor Factor from Human Glioblastoma Cells is a 12.5-kd Protein Closely Related to Transforming Growth Factor-β", *EMBO Journal* (1987) 6(6):1633–1636.

Segarini et al., "Extracellular domain of transforming growth factor-β (TGF-β) receptor type II encodes a soluble TGF-β binding protein when expressed in a bacterial system" *Molecular Biology of the Cell* (1992) 3:26A.

Andres et al., "Characteristics of membrane and soluble forms of the TGF-β binding proteoglycan, betaglycan" *Journal of Cellular Biochemistry* (1990) Supplemental 14E, p. 53.

Segarini et al., "The family of TGF-β receptors" *Journal of Cellular Biochemistry* (1991) Supplement 15F, p. 155.

Segarini et al., "The family of TGF-β receptors" *Journal of Cellular Biochemistry* (1991) Supplement 15F, p. 208.

Segarini et al., "Extracellular domain of transforming growth factor-β (TGF-β) receptor type II encodes a soluble TGF-β binding protein" *Journal of Cellular Biochemistry* (1993) Supplement 17E, p. 138.

Segarini et al., "Extracellular domain of transforming growth factor-β (TGF-β) recptor type II encodes a soluble TGF-β binding protein when expressed in a bacterial system" *Journal of Cellular Biochemistry* (1993) Supplement 17B, p. 81.

Buchner, J., et al., "Routes to active proteins from transformed microorganisms" *Current Opinion in Biotechnology* (1991) 2:532–538.

Schein, C.H., "Production of soluble recombinant proteins in bacteria" *Biotechnology* (1989) 7:1141–1149.

Butt, T.R., et al., "Ubiquitin fusion augments the yield of cloned gene products in *Escherichia coli*" *Proceedings of the National Academy of Sciences USA* (1989) 86:2540–2544.

Power, R.F., et al., "High level expression of a truncated chicken progesterone receptor in *Escherichia coli*" *Journal of Biological Chemistry* (1990) 265(3):1419–1424.

Hlodan, R., et al., "Protein folding and its implications for the production of recombinant proteins" *Biotechnology and Genetic Engineering Reviews* (1991) 9:47–88.

R. Wilder, et al., "Transforming Growth Factor-β in Rheumatoid Arthritis," *Annals of the New York Academy of Sciences*, 593:197–207 (1990).

G. Whalen, "Solid Tumours and Wounds: Transformed Cells Misunderstood as Injured Tissue?" *The Lancet*, 336:1489–1492 (Dec. 15, 1990).

M. Liu, et al., "Transforming Growth Factor-β—Mullerian Inhibiting Substance Family of Growth Regulators," *Cancer Investigation*, 9(3):325–336 (1991).

Gressner, A.M., et al (1994) *Ann. Biol. Clin.* (Parts) 52:205–226.

López–Casillas, F., et al. (1993) *Cell* 73: 1435–44.

Cheifetz, S., et al. (1992) *J. Biol. Chem.* 267(27): 19027–30.

López–Casillas, F., et al. (1991) Cell 67:785–95.

Smith, D.H., et al. (1987) Science 238:1704–07.

USES OF TGF-β RECEPTOR FRAGMENT AS A THERAPEUTIC AGENT

This application is a continuation of application Ser. No. 08/037,597, filed Mar. 26, 1993, now abandoned which is a continuation-in-part of application Ser. No. 07/968,375, filed Oct. 29, 1992, now abandoned.

DESCRIPTION

TECHNICAL FIELD

This invention relates to the fields of drug therapy and protein synthesis. A soluble TGF-β binding protein fragment is used to treat conditions characterized by an excess of TGF-β, including fibroproliferation and immunosuppression. The present invention also relates to recombinant expression of the binding protein fragment in prokaryotic and eukaryotic cells.

TECHNICAL BACKGROUND

Transforming growth factor-β (TGF-β) represents a family of polypeptides, of which three are present in mammals, TGF-β1, TGF-β2 and TGF-β3. These factors have global effects on cell growth and differentiation (Roberts and Sporn (1990) *Handbk. Exp. Pharm.* 95:419–58). There is a growing body of evidence that TGF-β also modulates the immune process (Wahl et al. (1989) *Immunol. Today* 10:258–61). In addition to stimulating the congregation of immune cells at the site of injury, TGF-β also provides strong positive feedback for its own continued synthesis (Kim et al. (1990) *Mol. Cell. Biol.* 10:1492–1497). These factors have led to the investigation of the role of TGF-β in immune and fibroproliferative disorders.

In fibroproliferative diseases, TGF-β is becoming considered as a prominent factor. TGF-β is known 1) to stimulate cells to produce more proteins, including collagen, biglycan, decorin and fibronectin; and 2) to inhibit enzymes which degrade these proteins. Thus, TGF-β can cause fibrous tissue to accumulate. For example, in diabetic nephropathy and human mesangial proliferative glomerulonephritis, both fibroproliferative diseases, a prominent and important pathological feature is the accumulation of mesangial matrix (Mauer et al. (1984) *J. Clin. Invest*, 74: 1143–55). Likewise, postradiation fibrosis is characterized by excessive TGF-β, proliferation of fibroblasts and overproduction of connective tissue (Canney and Dean (1990) *Brit. J. Radiol.* 63:620–23).

There have been several attempts to suppress the effects of TGF-β excess by administering antibody which is specific for TGF-β. In a pending patent application Ser. No. 759,109, filed Sep. 6, 1991, now U.S. Pat. No. 5,571,714 also assigned to Celtrix Pharmaceuticals, Inc., monoclonal antibodies to TGF-β were shown to have affinity constants ranging from $1.6 \times 10^7$ L/mol to $3.4 \times 10^8$ L/mol in a competitive radioimmunoassay test. These monoclonal antibodies were suggested for use in treating tumor cells that produce TGF-β to counteract the immunosuppressive effects of TGF-β. Another proposed use was treating metastatic cancers.

Border et al. (1990) *Nature* 346:371–74, found that antiserum against TGF-β suppressed experimentally induced glomerulonephritis, which was characterized by mesangial proliferation. Border et al. reported that the antibodies to TGF-β which were raised in rabbits had 50% binding to TGF-β at a ratio of 1:6000 in a radioimmunoassay. Antibodies typically have a molecular weight of at least 150 kilodaltons (kd).

More recently, Border et al. ((1992) *Kidney Int.* 41:566–570) mentioned that "[o]ther investigators have used our strategy of antagonizing TGF-β by administering anti-TGF-β in vivo. This approach has confirmed a causal role for TGF-β in pathological matrix accumulation by reducing scar formation in fetal skin, in the central nervous system following wounding and reduction of interstitial fibrosis in a model of acute lung injury." (p. 567) In a paper accepted for publication in *J. Exp. Med.*, Wahl also cites TGF-β excess in "a spectrum of connective tissue disorders including rheumatoid arthritis, scleroderma, myelofibrosis, and hepatic, intraocular, and pulmonary fibrosis."

Anti-TGF-β antibodies have been administered to animals given an intraarticular injection of bacterial cell walls in an amount sufficient to cause the development of arthritis. One intraarticular injection of anti-TGF-β was sufficient to prevent arthritis. (Wahl (1992) *J. Clin. Immunol.* 12:1–14). In the *J. Exp. Med.* paper, Wahl et al. reported that antibody injected into a joint before systemic administration of streptococcal cell wall (SCW) resulted in a 75% decrease in joint inflammation. Even if the antibody were injected about two weeks after the SCW injection, at which time the inflammation had become chronic, there was still a significant benefit. Likewise, Goddard et al. ((1990) *Cytokine* 2: 149–55) found that TGF-β inhibited the growth of cultured synovial cells, which was reversed by administration of neutralizing antibodies.

TGF-β-specific antibodies also were injected into the margins of healing dermal wounds in adult rats. Control wounds (those with irrelevant antibody or TGF-β) all had scarring, but the antibody-treated wounds healed completely with normal strength but no scar formation. Shah et al., (1992) *The Lancet* 339: 213–14.

TGF-β-specific antibody has also been found to partially restore, at least in laboratory tests, the defective T-cell responses due to excess TGF-β production such as in patients with acquired immune deficiency syndrome (AIDS). (Kekow et al. (1990) *Proc. Natl. Acad. Sci.* 87:8321).

In rat prostate cancer, TGF-β1 is overexpressed, compared to normal prostate tissue. It appears that TGF-β1 enhances tumor growth by stimulating tumor cells (Steiner and Barrack (1992) *Mol. Endocrinol.* 6:15–25). Steiner and Barrack tested the effect of anti-TGF-β antibody on overproducing prostate cancer cells which had stopped growing. The antibody caused the prostate cancer cells to begin proliferating again. In mouse prostate cancer, both TGF-β1 and 3 were elevated and were correlated with progression to malignancy and may even promote carcinoma (Merz et al. (1991) *Mol. Endocrinol.* 5:503–13).

Another way of suppressing TGF-β in experimental glomerulonephritis in rats, which is associated with TGF-β1 excess, was a low-protein diet. Both the excreted nitrogen and the expressed TGF-β1 decreased. (Okuda et al. (1991) *Proc. Natl. Acad. Sci. U.S.A.*, 88:9765–69.)

In addition, TGF-β has natural inhibitors, including decorin and endoglin. Yamaguchi et al. ((1990) *Nature* 346:281–84) have proposed that decorin binds TGF-β and provides negative regulation of the TGF-β by interfering with TGF-β binding to a receptor. Decorin is highly glycosylated and has a molecular weight of about 46 kd and an affinity for TGF-β of about $10^{-8}$ to $10^{-9}$M.

Endoglin also appears to bind TGF-β with an affinity constant of about $5 \times 10^{-11}$M. Endoglin also is highly glycosylated and has a molecular weight of about 90 kd.

Previously, anti-TGF-β, decorin and endoglin have been suggested as inhibitors of TGF-β. However, these three proteins share the undesirable feature of high molecular weight (20–180 kd). Affinity constants for the antibody and decorin are relatively low, ranging from about $10^{-8}$ to $10^{-9}$M. Moreover, administering antibodies from other species can cause cross-species reactions.

An improved inhibitor would have a much lower molecular weight and higher affinity. This combination of features would permit much lower doses and increase ease of administration. Moreover, a native protein would not cause cross-species reactions.

Nine classes of TGF-β receptors have been found. The main receptors on cells are Type I, Type II and Type III. A soluble form of the Type III receptor has been detected, and it binds TGF-β similarly to the membrane-bound Type III receptor (Andres et al. (1989) *J. Cell. Biol.* 109:3137–45).

The human Type II receptor has been cloned and codes for a protein of 563 amino acids (Lin et al. (1992) *Cell*, 68: 775–85). This protein contains three discreet domains: a 136-amino acid extracellular domain, a 30-amino acid hydrophobic transmembrane domain, and a 376-amino acid intracellular domain. The extracellular region binds TGF-β. The Type II receptor has a very high affinity for TGF-β, on the order of about $10^{-11}$ to $10^{-12}$M. Furthermore, the Type II receptor is a native human protein, which should help avoid cross-species reactions. And finally, the region which binds TGF-β is only about 100 amino acids long. Therefore, its molecular weight is only a fraction of previously suggested inhibitors.

Production of recombinant heterologous proteins in prokaryotic host cells is essential to produce commercially feasible amounts of protein. Unfortunately, bacterial host cells such as *E. coli* often are not ideal or simply cannot be used to produce such proteins. This is because the proteins, when over-expressed, form refractile, insoluble "inclusion bodies" and/or prove lethal to the cells. Inclusion bodies are found in the cytoplasm of the cell. Although inclusion bodies can be isolated from the cell by cell lysis and centrifugation, subsequent purification of the proteins involves dissolving the inclusion bodies and renaturing the proteins. Renaturation is not always effective or efficient. A variety of mechanisms have been sought to overcome these problems. However, none of the methods are ideal.

Purification of proteins produced in bacterial host cells has also proven to be problematic. In many cases, the proteins of interest, particularly when incorporated into inclusion bodies, co-purify with bacterial cell wall components which can be toxic.

Mammalian cells are sometimes preferred for recombinant production because they can appropriately glycosylate and properly fold proteins.

One method of simplifying the purification of such proteins is to produce them as a recombinant fusion protein. The protein to which the protein of interest is fused is one for which sophisticated purification schemes have been devised. For instance, in the case of ubiquitin fusion proteins, the fusion protein is purified by the well defined ubiquitin purification scheme, and the protein of interest is cleaved from ubiquitin by ubiquitin hydrolase. The ubiquitin is removed from the protein of interest by subtractive purification.

Although such fusion proteins improve purification of over-expressed proteins, they do not resolve the problems presented by proteins that form inclusion bodies upon expression or that cannot be expressed due to their lethality to the host cell.

International Publication No. WO 88/02406 to Bachmair et al. describes the importance of the amino terminal amino acid residue of the protein fused carboxy terminally to ubiquitin in ubiquitin fusion proteins. All amino acid residues with the exception of proline allow cleavage of ubiquitin from the fusion protein.

International Publication No. WO 89/12678 to Liu et al. describes a purification scheme for recombinant ubiquitin hydrolase. Ubiquitin hydrolase is useful in cleavage of ubiquitin from ubiquitin fusion proteins. The use of vectors encoding ubiquitin fusion proteins has been found to increase heterologous gene expression in yeast up to several hundred-fold. Ecker et al. (1989) *J. Biol. Chem.* 64:7715–7719.

Peptidyl-prolyl cis-trans isomerases (PPIs), catalyze rotation of the peptide bond on the amino side of proline residues and facilitates in vivo protein folding. One family of PPIs is termed "cyclophilins". Cyclophilins bind to the immunosuppressive agent cyclosporin A with high affinity resulting in cyclosporin A toxicity. Another PPI is FKBP which binds to the immunosuppressive agent FK506. Standaert et al. (1990) *Nature* 346:671–674. Yet another PPI is the yeast RBPI which bind to both rapamycin and FK506. Koltin et al. (1991) *Mol. Cell. Biol.* 11:1718–1723.

Cyclophilins are ubiquitous with homologous genes expressed in a variety of organisms including humans, rats, hamsters, yeast, *Neurospora crassa*, *Drosophila melanogaster* and tomatoes. Tomato cyclophilin genes expressed in *E. coli* were found mainly in inclusion bodies, but some activity was detected in the soluble fraction. Gasser et al. (1990) *Proc. Natl. Acad. Sci. USA* 87:9519–9523. Cloning and expression of a human cyclophilin in *E. coli* has also been reported. Holtzman et al. (1991) *J. Biol. Chem.* 266:2474–2479. Expression of a cloned human cyclophilin in *E. coli* has been shown to result in 40% of the cyclophilin in the soluble fraction. Liu et al. (1990) *Proc. Natl. Acad. Sci. USA* 87:2304–2308.

An *E. coli* PPI, termed "rotamase" has been found to be located in the periplasmic space where it is thought to function in refolding of secreted proteins. Liu and Walsh (1990) *Proc. Natl. Acad. Sci. USA* 87:4028–4032. Liu and Walsh cloned and over-expressed rotamase and found that although it is homologous to human cyclophilin, it is not sensitive to cyclosporin A.

The invention also is directed to recombinant DNA vectors and methods of use thereof. The vectors allow over-expression of TGF-β-binding receptor fragments in bacterial and mammalian host cells. The vectors contain a first gene encoding a protein of interest and a second gene encoding a peptidyl-prolyl cis-trans isomerase. Co-expression of the first and second genes allows over-expression of the protein of interest. In some cases the degree of solubility of the protein is also increased.

DISCLOSURE OF THE INVENTION

In one embodiment, the invention provides a method for treating an individual for a medical condition associated with TGF-β excess. The method provides for the parenteral, oral or local administration of a sufficient amount of TGF-β-binding receptor fragment to the individual to reduce excess TGF-β activity in the individual.

In another embodiment, the method of the present invention provides for the administration of a fragment of human recombinant TGF-β receptor.

In yet another embodiment, the method of the present invention provides for TGF-β receptor fragment administration by intravenous, intraocular, intraarticular, transdermal and enteral methods.

In another embodiment, the method of the present invention provides for the administration of the Type II TGF-β receptor. In another embodiment, the administered protein is a fragment of Type II TGF-β receptor. In a further embodiment, the administered protein is Type I TGF-β receptor; in another embodiment, the protein is a Type I TGF-β receptor fragment. In yet another embodiment, Type III TGF-β receptor fragment is administered.

In another embodiment, the TGF-β receptor fragment is administered to patients with cancer. In further embodiments, the type of cancer is plasmacytoma, glioblastoma, or prostatic or ovarian carcinoma.

In another embodiment of the present invention, the TGF-β receptor fragment is administered to patients with collagen vascular diseases, such as systemic sclerosis, polymyositis, scleroderma, dermatomyositis, or systemic lupus erythematosus.

In another embodiment of the present invention, the TGF-β receptor fragment is administered to patients with fibroproliferative disorders. In a further embodiment, the TGF-β receptor fragment is administered to patients with hepatic, intraocular and pulmonary fibrosis. In a further embodiment, the TGF-β receptor fragment is administered to patients with diabetic nephropathy, glomerulonephritis, proliferative vitreoretinopathy, rheumatoid arthritis, liver cirrhosis, and biliary fibrosis.

In still another embodiment, the method of the present invention provides for treating a wound in an individual to avoid excessive connective tissue formation which is associated with TGF-β excess. The method provides for administration of a sufficient amount of TGF-β-binding receptor fragment to the individual to reduce the excess of TGF-β in the individual. In further embodiments, the types of wounds include surgical incisions, trauma-induced lacerations and wounds involving the peritoneum for which the excessive connective tissue formation is abdominal adhesions. In a further embodiment, the excessive connective tissue formations which are avoided include scars, including those where the scar involves restenosis of blood vessels, and hypertrophic scars, and keloids.

In another embodiment of the present invention, the method provides for administration of TGF-β receptor fragment in the condition of TGF-β excess characterized by immunosuppression associated with an infectious disease. In a further embodiment, the immunosuppression may be associated with trypanosomal infection or viral infections such as human immunosuppression virus, human T cell lymphotropic virus (HTLV-1), lymphocytic choriomeningitis virus and hepatitis.

In another embodiment, the invention provides a method of increasing the effectiveness of a vaccine. In this aspect, TGF-β-binding receptor fragment is administered to an individual about to receive a vaccine or receiving a vaccine. The amount of TGF-β-binding receptor fragment is sufficient to increase the individual's immune response to the vaccine. In a preferred embodiment, the vaccinated individual is immunocompromised.

In another embodiment, the invention provides a method of preventing postradiation fibrosis in an individual undergoing or about to undergo radiation therapy. TGF-β-binding receptor fragment is administered in an amount sufficient to prevent excessive fibrous tissue formation.

The invention also is directed to recombinant DNA vectors and methods of use thereof. The vectors allow overexpression of TGF-β-binding receptor fragments in bacterial and mammalian host cells. The vectors contain a first gene encoding a protein of interest and a second gene encoding a peptidyl-prolyl cis-trans isomerase. Co-expression of the first and second genes allows over-expression of the protein of interest. In some cases the degree of solubility of the protein is also increased.

MODES FOR CARRYING OUT THE INVENTION

Figure 1:
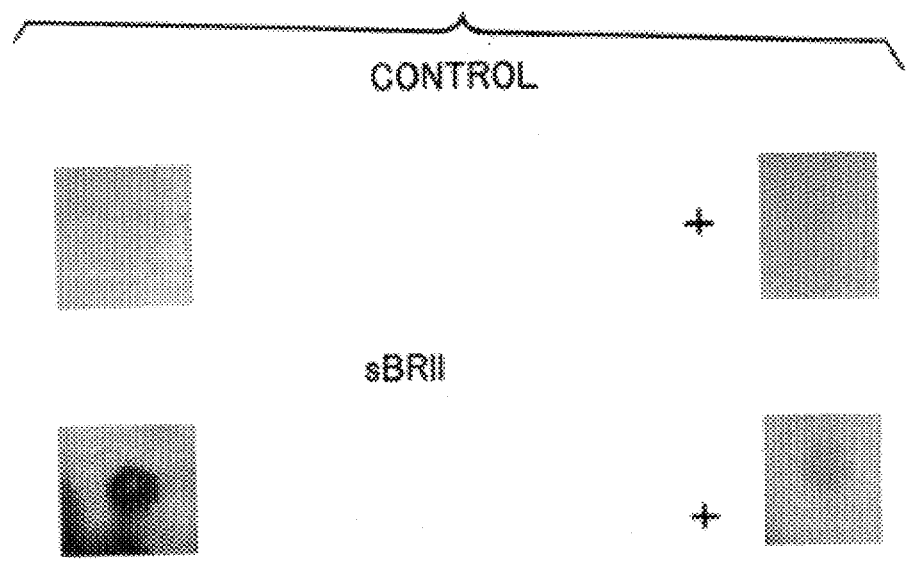
FIG. 1 is a photograph which illustrates binding of biotinylated TGF-β2 to filter paper embedded with Type II soluble TGF-β receptor fragment (sβ-RII).

The following terms are used herein:

"Individual" means a living organism, including humans, other mammals and any other animals which produce TGF-β.

"TGF-β" is a family of peptide growth factors, including five members, numbered 1 through 5.

"TGF-β excess" as used herein is an amount of TGF-β present in serum or tissue which is significantly above the normal level. More preferably, TGF-β excess is a level between about 2 and about 20 times normal. Even more preferably, TGF-β excess is a level between about 2 and about 15 times normal. For example, Deguchi measured 24-hour TGF-β production of bronchoalveolar cells and reported normal levels of 410±225 pg/$10^7$ cells against excess TGF-β production of 1288±453 pg/$10^7$ cells in systemic lupus erythematosus and 1417±471 pg/$10^7$ cells in scleroderma ((1992) Ann. Rheum. Dis. 51:362–65). TGF-β excess can be determined, in combination with normal levels, by measurement of the TGF-β protein, of TGF-β MRNA, or of products whose synthesis is stimulated by TGF-β, such as collagen.

TGF-β receptors are cell surface proteins, of which three (Type I, Type II and Type III) are known in mammals.

TGF-β receptor Type II is a membrane-bound protein with an intracellular domain, transmembrane domain and extracellular portion which binds to TGF-β. Human TGF-β receptor Type II has been determined to have the amino acid sequence shown in Lin et al., 1992, and corrected by personal communication as shown in SEQ ID NO:2.

A TGF-β receptor fragment is a portion or all of a TGF-β receptor molecule which is capable of binding TGF-β. Preferably, this fragment has a high affinity for TGF-β. Even more preferably, the TGF-β receptor fragment has a greater affinity for TGF-β than does anti-TGF-β antibody or decorin.

"sβ-RII" refers to protein fragments of the extracellular portion of the TGF-β receptor Type II which are soluble and bind with high affinity to TGF-β. Preferably, the affinity is in the range of about $10^{-11}$ to $10^{-12}$M, although the affinity may vary considerably with fragments of different sizes, ranging from $10^{-7}$ to $10^{-13}$M. These fragments are proteins consisting of about 136 amino acids or less. Most preferably, sβ-RII is about 136 amino acids.

In another embodiment, sβ-RII is about 10–110 amino acids in length and comprises the TGF-β binding site.

Preferably, the sβ-RII of this embodiment is a protein of about 50–80 amino acids.

If the entire native amino acid sequence of 136 amino acids is used, the amino acid sequence resembles that of the entire extracellular portion of the Type II receptor. When smaller sβ-RII fragments are employed, they resemble various portions of the extracellular portions of the Type II TGF-β receptor, so long as they bind TGF-β with high affinity.

Although the sequence of sβ-RII is based on the native TGF-β receptor II extracellular fragment, the definition of sβ-RII also comprises analogs of sβ-RII which have high affinity for TGF-β. Such analogs include those made by conservative substitutions of amino acids, as well as those made by mutated cells synthesizing sβ-RII. Only analogs with high affinity for TGF-β are included in this definition.

"Connective tissue" is fibrous tissue characterized by the presence of fibroblasts and fibrous proteins such as collagen and elastin.

A "therapeutic composition" as used herein is defined as comprising sβ-RII and other physiologically compatible ingredients. The therapeutic composition may contain excipients such as water, minerals and carriers such as protein.

"A sufficient amount of TGF-β-binding receptor fragment" as used herein refers to the amount of TGF-β receptor fragment that neutralizes the biologic activity of excess TGF-β. It may be determined by (1) suitable clinical variables of improvement, (2) pathologic evaluation of the effects on fibrosis and/or immunosuppression or prevention of fibrosis, or (3) a direct inhibition of TGF-β.

This invention provides for administering to an individual with a medical condition associated with TGF-β excess a sufficient amount of TGF-β-binding receptor fragment, such as sβ-RII, to reduce excess TGF-β activity in the individual. The TGF-β-binding receptor fragment is all or only a portion of a receptor which is capable of binding TGF-β. sβ-RII is made by synthesizing the extracellular domain of the TGF-β Type II receptor (β-RII) and developing a fragment of this β-RII domain as a high affinity, soluble binding protein (sβ-RII) for TGFβ. This invention further provides for delivering sβ-RII to a site where TGF-β is in excess, such as in disease states characterized by fibroproliferation and immunosuppression such as is associated with infectious disease.

The sβ-RII of the present invention may be synthesized by means known in the art. The longer, 136-amino acid version is preferably synthesized by recombinant techniques which are known to those in the art. Alternately, and preferably for shorter versions of sβ-RII, sβ-RII also can be synthesized by solid-phase synthetic methods known to those in the art.

While not wishing to be bound by any particular theory, it appears that the sβ-RII regulates TGF-β activity by competing for TGF-β with cell-surface receptors. It is further believed that sβ-RII inactivates TGF-β by removing it from the free pool of TGF-β available to interact with cell surface receptors. Depending on the pharmacologic properties of clearance, the sβ-RII/TGF-β complex is removed from the site of TGF-β excess. This complexing with excess TGF-β reduces the amount of free TGF-β. With less TGF-β available to complex with cell receptors, TGF-β induced fibroproliferation slows down, resulting in stasis of the disease state.

The sβ-RII fragments of the present invention may be used to treat viral infections in which there is an overproduction of TGF-β and immunosuppression. Examples of viruses with which TGF-β excess is associated include, but are not limited to, hepatitis C, lymphocytic choriomeningitis, human immunodeficiency virus (HIV), and human T cell lymphotropic virus (HTLV-1), the latter being discussed in Kim et al. ((1991) *Mol. Cell. Biol.* 11:5222–28).

The sβ-RII fragment of the present invention may be used to treat the trypanosome-mediated immunosuppression. This may be caused by *Trypanosoma cruzi* or *Leishmania cruzi*, among others. Immunosuppression in *Leishmania cruzi* has been studied by Barral-Netto et al., (1992) *Science* 257:545–48.

The sβ-RII of the present invention also may be used to increase the efficacy of vaccines. Because TGF-β may cause immunosuppression, the administration of sβ-RII can counteract immunosuppression caused by TGF-β and increase the vaccine recipient's immune response to the vaccine. sβ-RII should be particularly effective in immunosuppressed patients. sβ-RII may be administered before or concomitantly with the vaccine.

The sβ-RII fragments of the present invention also may be used to treat forms of cancer which are associated with excess TGF-β. It is also generally known that TGF-β is produced by different tumor cells (sarcomas and carcinomas). Specific examples of tumors in which TGF-β production is excessive include glioblastoma (Wrann et al. (1987) *EMBO. J.* 6: 1633–36; and Bodner et al. (1989) *J. Immunol.* 143: 3222–29) and plasmacytoma (Berg and Lynch, (1991) *J. Immunol.* 146: 2865–72). This TGF-β production may protect the tumor cells from recognition by the host's immune system, Wrann et al. (1987) *EMBO. J.* 6:1633. In these situations, TGF-β suppresses the proliferation of T and B cells, NK cells, LAK cells, and macrophages that are normally involved in tumor destruction. The sβ-RII fragments of the present invention also may be used to treat prostatic cancer. Merz et al. ((1991) *Mol. Endocrin.* 5:503–13) reported that elevated TGF-β is correlated with progression of prostatic hypertrophy to malignancy and to metastasis. Steiner and Barrack have also reported that overproduction of TGF-β1 prostatic tumors produced more extensive metastatic disease ((1992) *Mol. Endocrin.* 6:15–25)). Therefore, early treatment with sβ-RII may help abort progression to malignancy; and later treatment may prevent metastasis.

The administration of sβ-RII fragments of the present invention may be used in fibroproliferative disorders. As mentioned above, animal models of glomerulonephritis have shown good results with anti-TGF-β antibodies blocking excess TGF-β. These antibodies will be difficult to deliver because they have a high molecular weight and they may result in severe allergic reactions when they are derived from other species. Thus, it would be preferable to administer a lower molecular weight, native protein or close analog, such as sβ-RII, in glomerulonephritis. Kidney diseases associated with TGF-β excess include, but are not limited to, mesangial proliferative glomerulonephritis, crescentic glomerulonephritis, diabetic nephropathy, renal interstitial fibrosis, renal fibrosis in transplant patients receiving cyclosporin, and HIV-associated nephropathy. These conditions are associated with excessive fibrous tissue formation which administration of sβ-RII should suppress.

As sβ-RII by itself is not known to have an effect aside from capturing TGF-β, sβ-RII may safely be administered during or at the end of retinal reattachment surgery, which is the most common cause of proliferative vitreoretinopathy (PVR) (Connor et al. (1989) *J. Clin. Invest.* 83:1661–1666).

Another important fibroproliferative condition is rheumatoid arthritis (RA), which is also associated with excess TGF-β production. Data indicate that blocking TGF-β at any time in the development or chronic stages of RA may help stop the progressive deterioration of the joint and bone. Hence, sβ-RII fragments of the present invention may be administered to patients with early joint pain and to patients with prolonged joint pain and deteriorated joints. The current theory is that joint deterioration in RA is due to an overproduction of TGF-β. Excess TGF-β has been measured in joints after test animals are injected with streptococcal cell walls, whose presence is believed to cause RA. Because anti-TGF-β antibody blocks arthritic changes in this model, it is believed that sβ-RII may also have a positive effect.

Work in an animal model suggests that chronic liver cirrhosis which is characterized by excess collagen deposition, could be mediated by TGF-β. (Czaja et al. (1989) *J. Cell. Biol.*, 108: 2477–82; and Hoyt et al. (1988) *J. Pharm. Exp. Ther.* 246: 765). In patients with chronic hepatitis and cirrhosis, the levels of TGF-β1 mRNA were 2–14 times higher and correlated with higher measurements of serum procollagen than were observed in patients with normal or fatty livers. Six of eight patients with hepatitis C were treated with alpha-interferon for one year and had sustained clinical improvement and normalization of serum procollagen activity. These treated patients also had normal levels of TGF-β1 mRNA in liver biopsy specimens taken at the end of one year, further supporting the role of TGF-β in liver fibrosis (Castilla et al. (1991) *N. Engl. J. Med.* 324:933–40).

Cirrhosis of the liver is a widespread condition which is associated with an abnormally high degree of fibrous tissue in the liver and frequently with high levels of TGF-β. Cirrhosis is the end product of the liver's reaction to many types of injury, including alcohol abuse, exposure to other chemicals, infections (such as hepatitis), intestinal bypass operations and others. In cirrhosis, normal hepatocytes, which produce fibrous blood proteins and clear toxins from the blood, have been replaced by fibrous tissue. In many instances, TGF-β is in excess. In such instances, the sβ-RII fragment of the present invention may be used to treat cirrhosis.

sβ-RII fragments also may be used to treat biliary cirrhosis, a condition in which the bile ducts become scarred and interfere with the gall bladder emptying its enzymes and digestive juices into the small intestine and hence with the digestion of fats. sβ-RII fragments also may be of assistance in treating this condition when it is associated with excess TGF-β.

Other conditions associated with excess TGF-β levels include idiopathic pulmonary fibrosis and myelofibrosis. To complex with excess TGF-β and to slow the development of excess fibrous tissue, sβ-RII is intended for administration in these conditions.

The sβ-RII fragments of the present invention may be used to treat collagen vascular diseases that are associated with overproduction of TGF-β. It is currently believed that there is an overproduction of TGF-β in collagen vascular diseases, such as progressive systemic sclerosis (PSS), polymyositis, scleroderma, dermatomyositis, eosinophilic fascitis, and morphea. Collagen vascular diseases may also be associated with the occurrence of Raynaud's syndrome. Among other effects, excess TGF-β production may also be involved in interstitial pulmonary fibrosis, an end-stage lung disease which is associated with autoimmune diseases such as systemic lupus erythematosus (SLE) and scleroderma (Deguchi, (1992) *Ann. Rheum. Dis.* 51:362–65); or it may be caused by chemical contact, allergies to dust and hay fever. A therapeutically effective amount of the sβ-RII of this invention may be administered to neutralize the biologic activity of excess TGF-β, which in turn would prevent unwanted fibrosis.

sβ-RII fragments of the present invention also may be used in preventing excessive scarring in patients who are known to form keloids or hypertrophic scars. sβ-RII may be administered to prevent scarring or excessive scarring during healing of various types of wounds including surgical incisions and traumatic lacerations. sβ-RII may be applied to skin wounds before they are closed to help in healing without scar formation. sβ-RII also may be placed in surgical abdominal wounds to help prevent adhesion formation which occurs all too commonly after that type of surgery. Williams et al. ((1992) *J. Surg. Res.* 52:65–70) recently reported that TGF-β was more effective in promoting postoperative peritoneal adhesions than a control of diluent. Intraperitoneal injections of TGF-β for five days did not induce adhesions in unoperated rats. Williams et al. proposed that preventing TGF-β production postoperatively might help prevent adhesion formation. Rather than preventing TGF-β production, which could have systemic side effects, the present invention provides for the local administration of sufficient sβ-RII to complex with local TGF-β overproduction and prevent excessive healing processes.

According to Lindholm et al., ((1992) *J. Cell. Biol.* 117:395–400), TGF-β1 is a strong inhibitor of astrocyte proliferation and may thus interfere with nerve regeneration. Because sβ-RII complexes with TGF-β, sβ-RII may encourage nerve regeneration. In deeper wounds where nerves are cut, the application of sβ-RII also can help nerve regeneration.

TGF-β excess also has been reported in nasal polyposis, a condition characterized by multiple polyps (Ohno et al. (1992) *J. Clin. Invest.* 89: 1662–68). sβ-RII can help lower the TGF-β excess and slow the hyperproliferation that results in polyps. sβ-RII can be administered after polyp surgery to prevent excessive scarring and recurrence of polyps. sβ-RII can also be administered to inhibit polyp formation in the intestine.

sβ-RII may also be administered following coronary angioplasty, preferably placed along the inside of the affected arteries. According to Karas et al., ((1991) *Clin. Cardiol.* 14:791–801) restenosis or scarring and reclosing of arteries following coronary angioplasty is seen in approximately one-third of patients operated on. Because the fibrous network which ultimately develops into a scar normally accumulates rapidly, early administration of sβ-RII would reduce excess TGF-β in this area and slow excessive proliferation of connective tissue and restenosis.

TGF-β excess has also been observed in cardiac fibrosis after infarction and in hypertensive vasculopathy. To aid in proper healing without excess scar or fibrous tissue formation, sβ-RII can be administered in these conditions.

TGF-β excess also has been observed in the tissues of patients receiving radiation therapy. Such tissue is characterized by excess connective tissue development, epithelial thinning and blood vessel occlusion associated with overgrowth of endothelial cells. Administration of sβ-RII will complex with the excess TGF-β and will contribute to healing without excessive fibrosis.

Formulation, Administration and Dosage

The formulation, method of administration and dosage sβ-RII will depend upon the disorder to be treated, and the medical history of the patient. These factors are readily determinable in the course of therapy. Suitable patients with conditions caused by an excess of TGF-β can be identified by laboratory tests, medical history and physical findings. TGF-β excess can be determined directly by immunoassay (Example 10 below) of the patient's serum or of the affected tissue. Excess TGF-β can also be determined by bioassays such as the cell proliferation assay described in Kekow et al., (1990) *Proc. Natl. Acad. Sci. U.S.A.* 87: 8321–25. Excess TGF-β also can be determined indirectly by measuring the level of TGF-β mRNA (for example, in the polymerase chain reaction of Kekow et al.).

The medical history may reveal facts which support a diagnosis of fibroproliferative disorder, collagen vascular disease, immunosuppression, or of potential for problematic wound healing, as in peritoneal adhesions following surgery, or restenosis of blood vessels after coronary angioplasty. Conditions which are identified as being associated with high levels of TGF-β and/or proliferation of fibrous tissue are considered to cause TGF-β excess.

Patients may have a wide spectrum of physical findings which are indicative of such disorders. Skin biopsies have been used to test TGF-β in patients with systemic sclerosis. Swollen, hot joints are seen in arthritis.

In accordance with the method of the present invention, the formulation comprises sβ-RII in an administrable form. The method of the present invention provides for formulating sβ-RII in modes which are readily apparent to those skilled in the art. Preferably, the sβ-RII is dissolved in physiologically compatible carriers.

Physiologically compatible carriers for sβ-RII include intravenous solutions, such as normal saline, serum albumin, 5% dextrose, plasma preparations, other protein-containing solutions and TPN solutions. The preferred carrier for parenteral administration of sβ-RII is a sterile, isotonic aqueous solution, such as saline or 5% dextrose. Even more preferred is normal saline with human serum albumin. For use in enhancing the immune response to vaccines, sβ-RII may be mixed with the vaccine formulation.

Depending on the mode of administration, the sβ-RII composition may be in the form of liquid or semi-solid dosage preparations, such as for example, liquids, suspensions or the like. Alternatively, a solution of sβ-RII may be placed into an implant, such as an osmotic pump, for the slow release of sβ-RII over an extended period of time. Alternatively, sβ-RII may be provided in sustained release carrier formulations such as semi-permeable polymer carriers in the form of suppositories or microcapsules. See, for instance, U.S. Pat. No. 3,773,919 for Microcapsular Sustained Release Matrices Including Polylactides; Sidmon et al., *Biopolymers* 22 (1), 547–556 (1983) for copolymers of L-glutamic acid and γ-ethyl-L-glutamate; Langer et al., *J. Biomed. Res.* 15, 167–277 (1981) for poly(2-hydroxyethylmethacrylate) or the like. Finally, receptor fragmentation and modifications, such as fusion of the sβ-RII fragment with human immunoglobulin (IgG) or with polyethylene glycol (PEG) so as to extend the half life of the sβ-RII fragment, are other alternative forms of administration.

The mode of administration delivers sβ-RII to the individual in a safe, physiologically effective manner. sβ-RII may be given by intraocular, intranasal, subcutaneous, intravenous, intramuscular, intradermal, intraperitoneal, intraarticular, enteral or other conventional routes of administration.

In a preferred embodiment, the sβ-RII of the invention is administered locally to the affected tissue sites by bolus injection or perfusion. For example, for PVR, the preferred mode of administration is a single intraocular injection. Local administration is also preferred in peritoneal wounds to avoid adhesion formation and in other wounds to encourage healing with no keloids or visible scars. For nasal polyposis, nasal drops are preferred.

Local and systemic administration are equally preferred in lung fibrosis (parenteral injection or nasal spray or drops) and cancer. In early, localized tumors, localized administration may be preferred. In later tumor stages, where cancer cells may have metastasized, parenteral administration may be preferred, alone or in combination with local injection. RA can be treated by intraarticular or systemic administration.

Systemic administration is the preferred mode of administration in glomerulonephritis, liver cirrhosis, immunosuppressive conditions (such as viral infections, AIDS and trypanosomal infections), and in widespread skin diseases (such as progressive systemic sclerosis, diffuse fascitis, and generalized morphea). Systemic administration also is preferred when sβ-RII is used to enhance vaccine response. sβ-RII can be administered with the vaccine by subcutaneous, intramuscular or intradermal injection.

The dose of sβ-RII to be administered can be readily determined by those skilled in the art, based on the usual patient symptoms discussed above. The dosage of sβ-RII to be given in a bolus injection is preferred to be between 20 ng and 300 mg. The bolus injection may be repeated over several days, or the sβ-RII can be continuously infused. If given as an intravenous infusion, the amount of sβ-RII to be infused over a 24-hour period is about 1 mg to about 100 mg.

The amount of sβ-RII to administer may also be determined by maintaining the local tissue concentration of TGF-β at a subnormal level, or about 1–1,000 μg/ml. For tumors, the amount administered is preferably about 20 ng to 300 mg sβ-RII per gram tumor tissue.

Preferably, sβ-RII is applied topically, injected at the site of the problem or injected intravenously. Most preferably, sβ-RII is administered by bolus injection at the site where TGF-β is to be controlled. By intravenous injection, sβ-RII should be administered at a rate to maintain a circulating serum concentration sufficient to reduce the TGF-β excess.

Preferably, the patient is started with a relatively low dose of sβ-RII. The low dose preferably should be continued until the patient's acute phase is ameliorated or adequately improved, as indicated appropriate physical findings and laboratory results. Such improvement may be evident in two to three weeks. In the absence of significant improvement, the dose of sβ-RII should be increased.

For patients to be vaccinated, the dose of sβ-RII is preferably between 20 ng and 300 mg. Preferably, more sβ-RII is given to immunocompromised vaccinated patients. sβ-RII can be administered a short time before the vaccine, to permit sβ-RII to complex with TGF-β prior to vaccination. Or sβ-RII can be administered simultaneously with the vaccine.

Protein Synthesis

It has now been found that genes which could not previously be expressed or over-expressed in bacterial and mammalian host cells can now be expressed when coded for by vectors such as those described herein. Moreover, the over-expressed proteins also have increased solubility. The solubility can be further increased by ubiquition of the proteins.

The invention includes recombinant DNA vectors containing a first gene encoding TGF-β-binding receptor fragment and a second gene encoding a peptidyl-prolyl cis-trans isomerase. Concomitant expression of the first and second genes allows over-expression of sβ-RII.

The genes encoding the protein are preferably chimeric. That is, they encode a fusion protein. Preferably the chimeric genes encode a fusion protein containing ubiquitin and sβ-RII. More preferably, the chimeric gene encodes a ubiquitin-sβ-RII fusion protein.

The invention also includes methods for over-expressing sβ-RII in mammalian and bacterial hosts. The methods include expressing the gene encoding sβ-RII in the host cell and concomitantly expressing a gene encoding a peptidyl-prolyl cis-trans isomerase in the host cell. The cells can then be treated to remove sβ-RII, which can be subject to further purification techniques.

Preferably the host cells are a strain of E. coli, more preferably they are E. coli W3110DE3. The gene encoding sβ-RII is preferably chimeric. Preferably the chimeric gene encodes a fusion protein containing ubiquitin and sβ-RII. More preferably, the chimeric gene encodes a ubiquitin-sβ-RII fusion protein.

The invention further includes a method of producing a soluble, or more soluble, sβ-RII in a bacterial host. The methods include expressing the gene encoding sβ-RII in the host cell and concomitantly expressing a gene encoding peptidyl-prolyl cis-trans isomerase in the host cell. The cells can then be treated to remove sβ-RII, which can be subject to further purification techniques.

Preferably the host cells are a strain of E. coli, more preferably they are E. coli W3110DE3, which produces rotamase. The genes encoding sβ-RII is preferably chimeric. Preferably the chimeric gene encodes a fusion protein containing ubiquitin and sβ-RII. More preferably, the chimeric gene encodes a ubiquitin-sβ-RII fusion protein.

The invention has been disclosed by direct description. The following examples show that the sβ-RII binding protein fragment can treat conditions characterized by an excess of TGF-β; however, these examples should not be taken in any way as limiting the scope of the method.

EXAMPLES

Example 1 sβ-RII was expressed in E. coli as a 15 kd protein of 136 amino acids with no carbohydrate. Those skilled in the art are familiar with cloning genes in the fashion detailed in Lin et al. ((1992) Cell 68: 775–785) Lin et al. also disclose the complete amino acid and nucleotide sequences.

The expression vectors used in this work were prepared from pET3b supplied by W. Studier. A new vector, pETX, was prepared and differs from pET3b in that it contains a modified oligonucleotide linker downstream of the unique BamHI site in the vector, having the sequence 5' . . . GGATCCCGTGGAGGATTAAACCATG-GATGGATGCATAAGCTT CGAATTC . . . 3' (SEQ ID NO:3).

In addition, the restriction fragment between the unique EcoRI site and the EcoRV site downstream of the terminator was deleted so that both restriction sites were destroyed.

The pDJ12833 vector backbone was derived from pETX by reconstituting the tetracycline resistance gene and inserting a 385 bp fragment carrying the par locus of pSC101 (according to the method of Meacock and Cohen, (1980), Cell 20: 529–42) into the unique PvuII site of pBR322 backbone present in pET3b, the parent vector. pER10088 is similar to pDJ12833 but does not carry the par locus. Both vectors contain, in addition, the translational coupler described in Squires, et al. (1988) J. Biol. Chem. 263:16297–302.

The DNA encoding the extracellular domain of the type II receptor was subcloned after PCR amplification of the 136 codons of that domain from a pre-existing cDNA clone, pH2-3FF (obtained from MIT). The oligonucleotides used in the amplification were 5' . . . GGGGATCCGATAGTGGAG-GATGATTAAATGATCCCACCGCACGTTCAGAAGT . . . 3' (5' oligo) (SEQ ID NO:9); and 5'GGGGAATTCAAGCT-TAGTCAGGATTGCTGGTGT TATATTCTTCTGA . . . 3' (3' oligo) (SEQ ID NO:5). Amplification was for 40 cycles with annealing at 55° C. The single major product of this amplification was purified using the Mermaid Kit from Bio 101 (La Jolla, Calif.) and digested with BamHI and EcoRI, gel purified and ligated to pETX vector digested with the same enzymes+calf alkaline phosphatase. After transformation of JM109, the structure of a single recombinant plasmid (pDJ16902) was confirmed by DNA sequencing.

pDJ16905 was constructed in a similar fashion except that the 5' oligo for PCR amplification was 5 . . . GGGGC-CGCGGTGGTATCCCACCGCACGTTCA-GAAGTCGGTT . . . 3' (SEQ ID NO:6) and the enzymes used for subcloning were SacII and EcoRI. The vector used was pER10088 which contains the 76 codons for yeast ubiquitin configured to provide an in-frame fusion with the 136 codons of the Type II receptor extracellular domain.

pDJ16917 and pDJ16919 were constructed by transferring the expression cassettes from pDJ16905 and pDJ16902, respectively, into the backbone of expression plasmid pDJ12833.

pDJ16921 and pDJ16924 are identical to pDJ16917 and pDJ16919 (respectively) except for the addition of a modified gene for E. coli rotamase as a separate cistron immediately downstream of the stop codon following the 136 codons of the receptor extracellular domain.

The sβ-RII protein was obtained by growing E. coli strain W3110 DE3 containing pDJ16919 at 37° C. in a Biostat E fermentor (manufactured by Braun) and inducing sβ-RII synthesis. The cell paste was collected and stored at −80° C. until ready for use.

An aliquot of paste was suspended in 0.1M Tris pH 8.0, 5 mM EDTA, 1 mM PMSF. Lysozyme was added to a final concentration of 0.2 mg/ml and the sample incubated at 4° C. for approximately 30 min. The sample was sonicated with 3–60 sec pulses on ice on a Branson 250 Sonifier and centrifuged at 10,000 rpm on a Sorvall (Wilmington, Del.) centrifuge. The pellet was collected, and this fraction is known as the "inclusion body fraction".

The inclusion body fraction was solubilized in 6M guanidine HCl and dialyzed against 10 mMHCl. The dialyzate was neutralized with 1M NaOH and chromatographed on a Q-Sepharose column (Pharmacia, Piscataway, N.J.). The bound material was eluted with a salt gradient (0–0.5M sodium chloride) in 0.1M Tris pH 7.5 and the fractions were analyzed on 18% SDS-PAGE with Coomassie blue stain. The bulk of the sβ-RII appeared in fractions 5–15 and was pooled for analysis or further purification.

The sβ-RII protein prepared in this example was found to bind TGF-β when sβ-RII was bound to a hydrophobic support, as discussed in Example 2, and in solution as discussed in Example 3.

Example 2 sβ-RII had been previously solubilized from inclusion bodies in 6M guanidiumhydrochloride with 25 mM dithiothreitol. The sample was diluted five fold and split into two fractions. The "control" sample was left untreated. The "Sβ-RII" sample was brought to a final concentration of 5 mM cystamine and incubated overnight at 4° C. Both samples were dialized against 0.1M Tris, concentrated, and applied to a membrane for a ligand blotting assay as follows. First, Immobilon P membrane (Millipore Corp., Bedford Mass.) was soaked in methanol for five seconds and then in tris-buffered saline (50 mM Tris, pH 7.5, 0.2 NaCl) (TBS) for one to ten minutes. Meanwhile, the dot-blot apparatus (Gibco-BRL, Gaithersburg, Md.) was set up and the membrane inserted on top of a sheet of 3MM paper (Whatman International, Ltd., Maidstone, UK) wetted with TBS. This assembly was tightened.

Fifty μl TBS was placed in each well. Next, samples of SβRII and control were added in any volume up to 200 μl and vacuum filtered very slowly for about 5–15 minutes.

The assembly was disassembled, the filter was marked and blocked in TBS with 5% dried milk overnight at 4° C. It is important to start with a fresh TBS-milk suspension. Alternately, the filter could also be blocked for one hour at room temperature.

One blot was incubated with 50 pM biotinylated TGF-β2 (1.25 ng/ml) alone while the other blot was incubated with 50 pM biotinylated TGF-β2 and 50 nM TGF-β2(+) as a competing ligand for 1.5 hours at 37° C. Next the filter was washed three times, 10 minutes each with TBS/0.05% Tween 20. Next streptavidin-HRP (Zymed Laboratories, Inc., South San Francisco Calif.) was added at a dilution of 1:1000 in TBS/5% milk/0.05% Tween 20. This was incubated at room temperature for 30 minutes. The filter was washed three times, 10 minutes each with TBS/0.05% Tween 20.

The filter was moved to a new dish. It was overlaid with about 6 ml of a 1:1 mixture of ECL reagents (Amersham Corp., Arlington Heights, Ill.) and incubated for one minute.

The filter paper was blotted on a paper towel and was placed in a plastic bag and sealed. The filter was exposed to film (XAR-5, Eastman Kodak, Rochester, N.Y.) for one to 45 minutes.

The results of the sβ-RII fragment binding to biotinylated TGF-β2 bound to filter paper are shown in FIG. 1.

Example 3

Figure 2A:
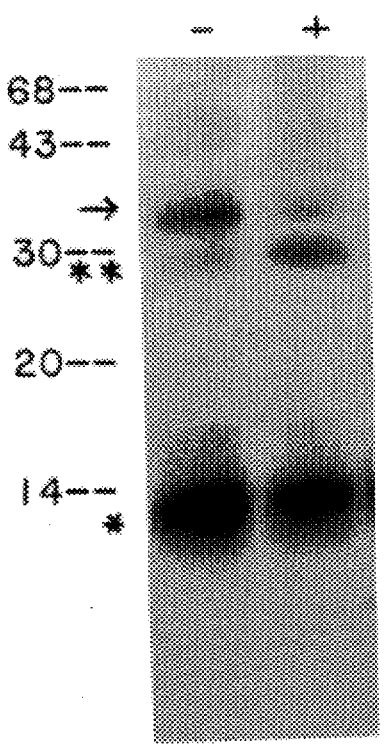
FIGS. 2a and 2b are photographs of electrophoresis results showing that sβ-RII from $E.$ $coli$ and COS cells, respectively, binds with specificity to TGF-β in solution.

This example demonstrates that sβ-RII binds with TGF-β in solution. Q-Sepharose bound material (804 μg/ml) was incubated overnight at 4° C. with 50 pM $^{125}$I-TGF-β1 without (−) or with (+) 40 nM unlabeled TGF-β1. The complexes were cross-linked at 4° C. for 15 min with 0.3 mM disuccinimidyl suberate and electrophoresed under reduced conditions on 18% SDS-PAGE. The gel was dried and complexes were visualized by autoradiography. FIG. 2 is a photograph of these results. Molecular size standards are indicated at the left in kilodaltons. The "*" indicates monomeric TGF-β1; the "**" indicates dimeric TGF-β1; the "→" indicates the appropriate size complex at approximately 31 kD (monomer of TGF-β cross-linked to sβ-RII).

Example 4

Plasmid H2-3FF containing a 4.5 kb cDNA fragment of the human TGF-β type II receptor (Lin et al., (1992) Cell, 68:775–85) was cloned into the EcoRI site of TGF-β plasmid pcDNAI was digested with EcoRI. The 4.5 kb cDNA fragment was isolated and subcloned into the EcoRI site of plasmid BlueScript SKII$^+$. The plasmid obtained from this subcloning experiment was named BS/βRII RI. This plasmid was used to transform E. coli strain CJ236 to obtain single-stranded DNA containing uracil residues (UssDNA). Single-stranded uracil-containing DNA was isolated by infecting CJ236 cells containing plasmid BS/βRII RI with helper phage VCS-M13 and subsequent kanamycin selection. The UssDNA obtained from these cultures was to be used as a template for site-directed mutagenesis experiments.

An oligonucleotide was synthesized with the antisense sequence of the TGF-β type II receptor from nucleotides 553–583 (nucleotides are numbered according to Lin et al., 1992) with the exception of the codon for Asn$^{106}$ which was changed such that a stop codon would be inserted. The sequence of the oligonucleotide used to create this mutation is 5'-TAGCAACAAGTCAGGTTAGCTGGTGTTATATTC-3' (SEQ ID NO:7). This primer in combination with the UssDNA described above was used to carry out an in vitro mutagenesis experiment (Kunkel et al., (1985) Proc. Natl. Acad. Sci. USA 82:488–492). Clones containing the desired mutation were identified by nucleotide sequencing. A clone containing a stop codon in place of Asn$^{106}$ was named BS/βRIIs.

BS/βRIIS plasmid DNA was purified and digested with EcoRI and BglII to isolate a 1177 base pair fragment comprising the 5' untranslated sequence and sequences for the extracellular domain (ECD) of the receptor, and a portion of the transmembrane domain containing the stop codon created by site-directed mutagenesis. This 1177 base pair EcoRI-BglII fragment was subcloned into the EcoRI-BglII site of plasmid pSG5 (Stratagene). This plasmid allows expression of heterologous genes in mammalian cells utilizing a SV$_{40}$ early promoter and SV$_{40}$ splice and polyadenylation signals. The plasmid created by this subcloning experiment was called pSG/βRIIs.

Example 5

COS-M6 cells were maintained in DMEM high glucose media supplemented with 10% fetal bovine serum and antibiotics. COS-M6 cells were transiently transfected using the DEAE-dextran method as described by Seed et al. (1987) Proc. Natl. Acad. Sci. USA 84:3365–3369. Briefly, plasmids pSG/βRIIs or pSG5 (negative control) were complexed with DEAE-dextran and added to the cultures for 2 hours. Following this incubation, the cells were glycerol shocked, washed and then allowed to recover for 32 hours. The cultures were then washed three times with serum-free media and allowed to grow for an additional 72 hours in serum-free media. The media were collected, the cell debris was removed by centrifugation and then analyzed for the presence of soluble TGF-β type II receptor expression.

Example 6

Figure 2B:
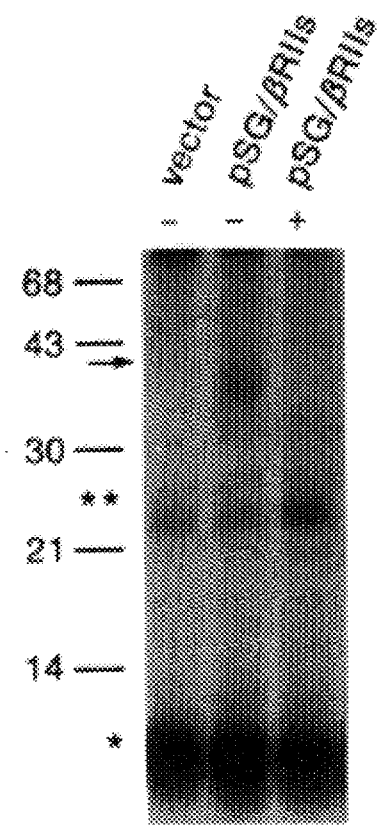
Figure 3A:
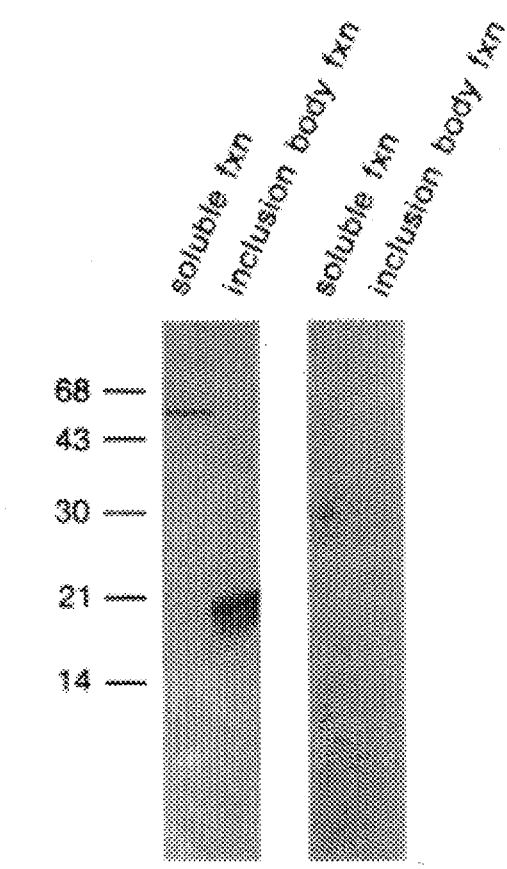
FIGS. 3a and 3b show the reaction of antibody specific for a fragment of the sβ-RII with $E.$ $coli$ soluble and inclusion body fractions (FIG. 3a) and with COS supernatants (FIG. 3b) transfected with control vector (right lane) or sβ-RII vector (left lane).
Figure 3B:
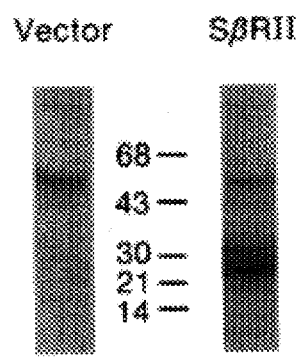

Initially the soluble type II receptor protein (sβ-RII) was detected by visualization on a Western blot. Supernatants were electrophoresed under reducing conditions on SDS-PAGE and blotted (Towbin et al., (1979) Proc. Natl. Acad. Sci. USA 76:4350–4354). Polyclonal rabbit antisera prepared against a peptide (residues 68–89) were incubated with the blot and the immunoreactive proteins were visualized after developing with an alkaline phosphatase conjugated anti-rabbit IgG and Nitro blue tetrazolium (FIGS. 3a and 3b). See Example 10 for more detail on the antisera preparation. The peptide antisera detect a single protein from E. coli (FIG. 3a) and a heterogeneous set of proteins ranging in size from 24–32 kDa from COS cells (FIG. 3b). Binding of radiolabeled TGF-β to proteins expressed by transfected COS-M6 cells was performed essentially as described previously (Segarini et al. (1989) *Mol. Endocrinol.* 3:261–272). Briefly, purified TGF-β was radiolabeled with Na$^{125}$I and incubated with aliquots of the conditioned media from cells transfected with either plasmid pSG/βRIIs or pSG5 as a negative control. Following affinity labeling, TGF-β/soluble receptor complexes were covalently crosslinked with disuccinimidyl suberate, separated by reducing SDS-PAGE and visualized by autoradiography. Included in some of the binding reactions was a 1000-fold molar excess of unlabeled TGF-β to compete for binding with radiolabeled material. FIG. 2B is the result of such a binding experiment demonstrating the presence of an affinity labeled protein of approximately 40 kda that was not present in vector-only transfected cells. Binding of radiolabeled TGF-β1 could be effectively blocked by including a 1000-fold molar excess of unlabeled TGF-β1 (FIG. 2B), lane labeled pSG/βRIIs$^+$) but not TGF-β2 (data not shown) in the binding reaction mixture.

Example 7

The effect of sβ-RII is compared with that of anti-TGF antibody in a glomerulonephritis model. Experimental glomerulonephritis can be induced in rats with a single injection of antithymocyte serum because the glomerular mesangial cells express a thy-1.1 epitope on their surfaces. The experimental lesion is acute mesangial proliferative glomerulonephritis and is characterized by expansion of the mesangial matrix and hypercellularity. The injured cells also express more TGF-β1 mRNA and TGF-β1, which in turn stimulates the synthesis of two proteoglycans, biglycan and decorin.

The antiserum is prepared by immunizing a rabbit with a cyclized, synthetic peptide containing residues 78–109 of human TGF-β1. The anti-TGF-β1 antiserum is capable of inhibiting binding of TGF-β to cells. (Flanders et al. (1988) *Biochemistry* 27:739–46)

First, glomerulonephritis is induced in rats by an intravenous injection of antithymocyte serum. Next, for six days, three groups of rats are treated with daily intravenous injections of saline (the negative control group), anti-TGF-β1 antiserum (the positive control group) or sβ-RII.

On the seventh day, the animals are sacrificed and slides are made of the kidneys, which are stained with periodic acid-Schiff solution to emphasize the pathological changes. The negative control kidneys have full-blown glomerulonephritis with reddish-pink amorphous fibrous material filling most of the glomerulus. The positive control kidneys have a staining pattern which is similar to a normal glomerulus. The kidney which is treated with sβ-RII also has a normal appearance, indicating that the sβ-RII blocks the response due to the secretion of excessive TGF-β.

The extent of glomerular injury can be quantitated by performing glomerular cell counts from 30 randomly selected glomeruli from normal animals and nephritic animals in each group. On day 4, there are fewer cells in glomeruli from antithymocyte-treated rats, presumably because the treatment causes cell lysis. By day 7, there are more cells than normal. The changes in cell counts in the anti-TGF-β1 and sβ-RII group are expected to be the same.

Another measure of the effect of anti-TGF-β1 and sβ-RII on the disease process is to quantitate the amount of extracellular matrix accumulation in the glomeruli. The degree of glomerular matrix expansion is determined as the percentage of each glomerulus occupied by the mesangial matrix according to the method of Raij et al. (1984) *Kidney Int.* 26: 137–43. The anti-TGF-β1 and sβ-RII kidneys are expected to have similar percentages of mesangial matrix to that in normal kidney, and significantly less mesangial matrix than in the negative control kidneys.

After glomerular injury and simultaneous treatment with anti-TGF-β, the mesangial cells expressed more TGF-β1 mRNA; however, proteoglycan synthesis is nearly normal with anti-TGF-β1 and sβ-RII.

Example 8

The following compares the action of TGF-β antibody with sβ-RII in an arthritis model. TGF-β antibody is prepared as disclosed in U.S. Pat. No. 5,571,714, which is incorporated by reference in its entirety. This application discloses the formation of monoclonal antibodies 3C7.14 specific for TGF-β2 and TGF-β3 and 1D11.16 specific for TGF-β1, -β2 and -β3.

First, arthritis is induced in pathogen-free female LEW rats (Harlan Sprague Dawley, Indianapolis, Ind.) weighing about 100 grams. Each receives a dose of cell wall fragments from Group A streptococci (SCW) (30 μg rhamnose/gm bodyweight), injected intraperitoneally (ip) according to the technique described in Brandes et al. (1991) *J. Clin. Invest.* 87:1108.

SCW-injected and control LEW rats are given an intraarticular (IA) injection in one of the hind ankles of one of the following:

1. anti-TGF-β (1D11.16) which is specific for TGF-β1 and TGF-β1 in 25 μl PBS,
2. sβ-RII in 25 μl PBS,
3. PBS only, or
4. an irrelevant isotype control mouse myeloma immunoglobulin (MOPC21, IgG$_1$)

Joints are clinically monitored by determining the amount of joint erythema, swelling and distortion on a scale of 0 (normal) to 4 (severe inflammation). Radiographs are taken and are evaluated for soft tissue swelling, joint space narrowing, bone erosions and deformity. Tissue specimens are obtained and prepared for histopathologic analysis as described in Brandes et al., ibid. Total RNA is isolated from excised synovial tissues according to the method of Allen et al. (1990) *J. Exp. Med.* 171:231.

Injection of SCW produces an acute inflammatory response which is clinically detectable within hours and maximal in 3–5 days. When anti-TGF-β is injected directly into a joint before ip administration of the SCW, inflammation at 24 hours is significantly below that observed in joints with the irrelevant antibody. At the peak of the acute response, inflammation of anti-TGF-β joints remains far below that of joints with the irrelevant antibody. Even if joints are injected with anti-TGF-β when inflammation is well developed (day 13), anti-TGF-β still has a significant anti-inflammatory effect, when compared to irrelevant antibody. Because sβ-RII also binds TGF-β, sβ-RII has a similarly beneficial effect when given early or late in the inflammatory process.

Example 9

To simulate acute liver injury, the hepatotoxin, D-galactosamine, is administered to cause liver fibrosis, mortality, and maximal TGF-β gene expression approximately 48 hours after administration. A rat model utilizing this hepatotoxin is used to evaluate the therapeutic effect of sβ-RII on acute liver fibrosis and serves as a model for liver cirrhosis.

Sprague-Dawley rats are administered 1.6 g/kg D-galactosamine intraperitoneally. Half of the rats are also to be given sβ-RII two hours prior to D-galactosamine administration, and at 24, 48, and 72 hours after D-galactosamine administration. Two rats from each test group are sacrificed at 48 hours to evaluate the efficacy of sβ-RII at peak TGF-β gene expression.

Histological examination reveals that sβ-RII-treated animals exhibit reduced liver pathology. Northern blot evaluation of tissues from specimens treated with sβ-RII show significantly decreased levels of collagen mRNA and almost normal levels of serum albumin, in contrast to non-treated controls.

Example 10

Polyclonal antibodies to the carboxy-terminal region of sβ-RII have been prepared and tested. Linear or cyclic peptides of amino acids 68–89 were injected once per month (in one case a month was skipped) at a concentration of 4 mg/ml in phosphate buffered saline with 200 μl per injection in complete Freund's adjuvant (first injection) or incomplete Freund's adjuvant (succeeding boosts). Bleeds were collected during the second, fourth, fifth, sixth, and seventh months after the initial boost.

Soluble and inclusion body fractions from *E. coli*, and supernatant fractions from sβ-RII and vector-transfected COS cells were electrophoresed under reducing conditions on SDS-PAGE. The *E. coli* fractions were prepared in duplicate. The proteins were electrotransferred to Immobilon P filters (Millipore, Bedford Md.). Next, the *E. coli* filters were blocked with super-Blotto (2.5% nonfat dry milk in Tris buffered saline (TBS), 10% (v,v) glycerol, 1M glucose, 0.5% Tween 20). The COS filters were blocked with standard Blotto (5% nonfat dry milk in Tris buffered saline). Then all filters were reacted with 10 μg/ml of rabbit antiserum. One half of the duplicate *E. coli* filters was incubated with nonimmune rabbit antiserum as a control. The blots were washed with TBS, containing 0.05% Tween 20 (T-TBS), and reacted with a secondary antibody, goat anti-rabbit IgG horseradish peroxidase (HRP) diluted 1:50,000, and incubated for one hour. The blot was washed with T-TBS and reacted with a membrane TMB kit for Kirkegaard and Perry according to package directions.

FIG. 3a shows *E. coli* soluble and inclusion body fractions reacted with peptide antiserum (left lane) or with control rabbit antisera (right lane). FIG. 3b shows COS supernatants from cells transfected with control vector (right lane) or sβ-RII vector (left lane). sβ-RII produced in COS cells is glycosylated and appears as heterogeneous bands.

In both *E. coli* and COS systems, a soluble receptor was produced and included an amino acid sequence that is recognized by antisera induced by linear and/or cyclic peptides of amino acids 68–89 of the extracellular domain of the type II TGF-β receptor. Control nonimmune rabbit antiserum did not recognize the type II receptor. Vector-transfected COS cells did not produce a protein that is reactive with the antisera.

COS cells were transfected with the pSG/βRII vector or with a control vector (pSG5). After 72 hours, the two supernatants were collected, incubated with 50 pM $^{125}$I-TGF-β1 without (−) or with (+) 40 nM unlabeled TGF-β1. The samples were crosslinked with 0.3 mM disuccinimidyl suberate (DSS) (Pierce Chemical Co., Rockford Ill.) and electrophoresed on SDS-PAGE under reducing conditions. The gels were dried and exposed for autoradiography, with the result shown in FIG. 4. A single asterisk (*) indicates monomeric TGF-β1, a double asterisk indicates dimeric TGF-β1 and a single arrowhead indicates the TGF-β1/sβ-RII complex. The size and heterogeneous appearance of the complex suggests that the sβ-RII from COS cells is glycosylated with 7–10 kD of carbohydrate.

Example 11

The efficacy of TGF-β in preventing post-radiation fibrosis can be assessed in patients who require radiation therapy for a tumor, such as adenocarcinoma, prior to bowel resection. At surgery, biopsies of various tissues can be obtained. There are two negative control groups: patients who do not receive radiotherapy prior to surgery and patients who receive radiotherapy but no TGF-β. The study group is administered sβ-RII concomitantly with the radiotherapy.

Each day, when the patient reports for radiotherapy, the patient receives an intravenous injection of sβ-RII. After radiation therapy is stopped, the patient receives weekly intravenous doses of sβ-RII until surgery.

At surgery, the tumor and associated tissues are removed. Slides are made from the tumor and tissue samples. Under microscopic examination, the tissue samples show signs of healing without excessive fibrosis.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

---

We claim:

1. A method for treating an individual for a medical condition associated with TGF-β excess comprising the step of administering to the individual a high affinity type II TGF-β-binding receptor fragment having the sequence shown as amino acids 1–105 of SEQ ID NO: 2 in an amount sufficient to reduce the activity of TGF-β in said individual.

2. The method of claim 1 wherein the TGF-β receptor fragment is administered by a method selected from the group consisting of intravenous, intraocular, intraarticular, transdermal, and enteral administration.

3. The method of claim 1 wherein said medical condition comprises a fibroproliferative disorder.

4. The method of claim 3 wherein said fibroproliferative disorder comprises a fibrosis selected from the group consisting of hepatic, kidney, intraocular, and pulmonary fibrosis.

5. The method of claim 3 wherein said fibroproliferative disorder is selected from the group consisting of diabetic nephropathy, glomerulonephritis, proliferative vitreoretinopathy, liver cirrhosis, biliary fibrosis, and myelofibrosis.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2095 base pairs
        ( B ) TYPE: nucleic acid
        ( C ) STRANDEDNESS: double
        ( D ) TOPOLOGY: linear -continued (ii) MOLECULE TYPE: DNA (genomic)

(ix) FEATURE:
  (A) NAME/KEY: CDS
  (B) LOCATION: 341..2041

(xi) SEQUENCE DESCRIPTION: SEQ ID NO:1:

```
CGCTCGTTGG CGAGGAGTTT CCTGTTTCCC CCGCAGCGCT GAGTTGAAGT TGAGTGAGTC        60

ACTCGCGCGC ACGGAGCGAC GACACCCCCG CGCGTGCACC CGCTCGGGAC AGGAGCCGGA       120

CTCCTGTGCA GCTTCCCTCG GCCGCCGGGG GCCTCCCCGC GCCTCGCCGG CCTCCAGGCC       180

CCTCCTGGCT GGCGAGCGGG CGCCACATCT GGCCCGCACA TCTGCGCTGC CGGCCCGGCG       240

CGGGGTCCGG AGAGGGCGCG GCGCGGAGCG CAGCCAGGGG TCCGGGAAGG CGCCGTCCGT       300

GCGCTGGGGG CTCGGTCTAT GACGAGCAGC GGGGTCTGCC ATG GGT CGG GGG CTG        355
                                              Met Gly Arg Gly Leu
                                                1               5

CTC AGG GGC CTG TGG CCG CTG CAC ATC GTC CTG TGG ACG CGT ATC GCC        403
Leu Arg Gly Leu Trp Pro Leu His Ile Val Leu Trp Thr Arg Ile Ala
         10                  15                  20

AGC ACG ATC CCA CCG CAC GTT CAG AAG TCG GTT AAT AAC GAC ATG ATA        451
Ser Thr Ile Pro Pro His Val Gln Lys Ser Val Asn Asn Asp Met Ile
             25                  30                  35

GTC ACT GAC AAC AAC GGT GCA GTC AAG TTT CCA CAA CTG TGT AAA TTT        499
Val Thr Asp Asn Asn Gly Ala Val Lys Phe Pro Gln Leu Cys Lys Phe
         40                  45                  50

TGT GAT GTG AGA TTT TCC ACC TGT GAC AAC CAG AAA TCC TGC ATG AGC        547
Cys Asp Val Arg Phe Ser Thr Cys Asp Asn Gln Lys Ser Cys Met Ser
     55                  60                  65

AAC TGC AGC ATC ACC TCC ATC TGT GAG AAG CCA CAG GAA GTC TGT GTG        595
Asn Cys Ser Ile Thr Ser Ile Cys Glu Lys Pro Gln Glu Val Cys Val
 70                  75                  80                  85

GCT GTA TGG AGA AAG AAT GAC GAG AAC ATA ACA CTA GAG ACA GTT TGC        643
Ala Val Trp Arg Lys Asn Asp Glu Asn Ile Thr Leu Glu Thr Val Cys
                 90                  95                 100

CAT GAC CCC AAG CTC CCC TAC CAT GAC TTT ATT CTG GAA GAT GCT GCT        691
His Asp Pro Lys Leu Pro Tyr His Asp Phe Ile Leu Glu Asp Ala Ala
             105                 110                 115

TCT CCA AAG TGC ATT ATG AAG GAA AAA AAA AAG CCT GGT GAG ACT TTC        739
Ser Pro Lys Cys Ile Met Lys Glu Lys Lys Lys Pro Gly Glu Thr Phe
         120                 125                 130

TTC ATG TGT TCC TGT AGC TCT GAT GAG TGC AAT GAC AAC ATC ATC TTC        787
Phe Met Cys Ser Cys Ser Ser Asp Glu Cys Asn Asp Asn Ile Ile Phe
     135                 140                 145

TCA GAA GAA TAT AAC ACC AGC AAT CCT GAC TTG TTG CTA GTC ATA TTT        835
Ser Glu Glu Tyr Asn Thr Ser Asn Pro Asp Leu Leu Leu Val Ile Phe
150                 155                 160                 165

CAA GTG ACA GGC ATC AGC CTC CTG CCA CCA CTG GGA GTT GCC ATA TCT        883
Gln Val Thr Gly Ile Ser Leu Leu Pro Pro Leu Gly Val Ala Ile Ser
                 170                 175                 180

GTC ATC ATC ATC TTC TAC TGC TAC CGC GTT AAC CGG CAG CAG AAG CTG        931
Val Ile Ile Ile Phe Tyr Cys Tyr Arg Val Asn Arg Gln Gln Lys Leu
             185                 190                 195

AGT TCA ACC TGG GAA ACC GGC AAG ACG CGG AAG CTC ATG GAG TTC AGC        979
Ser Ser Thr Trp Glu Thr Gly Lys Thr Arg Lys Leu Met Glu Phe Ser
         200                 205                 210

GAG CAC TGT GCC ATC ATC CTG GAA GAT GAC CGC TCT GAC ATC AGC TCC       1027
Glu His Cys Ala Ile Ile Leu Glu Asp Asp Arg Ser Asp Ile Ser Ser
     215                 220                 225

ACG TGT GCC AAC AAC ATC AAC CAC AAC ACA GAG CTG CTG CCC ATT GAG       1075
Thr Cys Ala Asn Asn Ile Asn His Asn Thr Glu Leu Leu Pro Ile Glu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|                           |     | 230 |     |     |     | 235 |     |     |     | 240 |     |     |     | 245 |     |      |
| CTG | GAC | ACC | CTG | GTG | GGG | AAA | GGT | CGC | TTT | GCT | GAG | GTC | TAT | AAG | GCC | 1123 |
| Leu | Asp | Thr | Leu | Val | Gly | Lys | Gly | Arg | Phe | Ala | Glu | Val | Tyr | Lys | Ala |      |
|     |     |     |     | 250 |     |     |     | 255 |     |     |     |     |     | 260 |     |      |
| AAG | CTG | AAG | CAG | AAC | ACT | TCA | GAG | CAG | TTT | GAG | ACA | GTG | GCA | GTC | AAG | 1171 |
| Lys | Leu | Lys | Gln | Asn | Thr | Ser | Glu | Gln | Phe | Glu | Thr | Val | Ala | Val | Lys |      |
|     |     |     |     | 265 |     |     |     | 270 |     |     |     |     | 275 |     |     |      |
| ATC | TTT | CCC | TAT | GAG | GAG | TAT | GCC | TCT | TGG | AAG | ACA | GAG | AAG | GAC | ATC | 1219 |
| Ile | Phe | Pro | Tyr | Glu | Glu | Tyr | Ala | Ser | Trp | Lys | Thr | Glu | Lys | Asp | Ile |      |
|     |     |     | 280 |     |     |     | 285 |     |     |     |     | 290 |     |     |     |      |
| TTC | TCA | GAC | ATC | AAT | CTG | AAG | CAT | GAG | AAC | ATA | CTC | CAG | TTC | CTG | ACG | 1267 |
| Phe | Ser | Asp | Ile | Asn | Leu | Lys | His | Glu | Asn | Ile | Leu | Gln | Phe | Leu | Thr |      |
|     |     | 295 |     |     |     | 300 |     |     |     | 305 |     |     |     |     |     |      |
| GCT | GAG | GAG | CGG | AAG | ACG | GAG | TTG | GGG | AAA | CAA | TAC | TGG | CTG | ATC | ACC | 1315 |
| Ala | Glu | Glu | Arg | Lys | Thr | Glu | Leu | Gly | Lys | Gln | Tyr | Trp | Leu | Ile | Thr |      |
| 310 |     |     |     |     | 315 |     |     |     | 320 |     |     |     |     | 325 |     |      |
| GCC | TTC | CAC | GCC | AAG | GGC | AAC | CTA | CAG | GAG | TAC | CTG | ACG | CGG | CAT | GTC | 1363 |
| Ala | Phe | His | Ala | Lys | Gly | Asn | Leu | Gln | Glu | Tyr | Leu | Thr | Arg | His | Val |      |
|     |     |     |     | 330 |     |     |     | 335 |     |     |     |     | 340 |     |     |      |
| ATC | AGC | TGG | GAG | GAC | CTG | CGC | AAG | CTG | GGC | AGC | TCC | CTC | GCC | CGG | GGG | 1411 |
| Ile | Ser | Trp | Glu | Asp | Leu | Arg | Lys | Leu | Gly | Ser | Ser | Leu | Ala | Arg | Gly |      |
|     |     |     | 345 |     |     |     | 350 |     |     |     |     | 355 |     |     |     |      |
| ATT | GCT | CAC | CTC | CAC | AGT | GAT | CAC | ACT | CCA | TGT | GGG | AGG | CCC | AAG | ATG | 1459 |
| Ile | Ala | His | Leu | His | Ser | Asp | His | Thr | Pro | Cys | Gly | Arg | Pro | Lys | Met |      |
|     |     | 360 |     |     |     | 365 |     |     |     |     |     | 370 |     |     |     |      |
| CCC | ATC | GTG | CAC | AGG | GAC | CTC | AAG | AGC | TCC | AAT | ATC | CTC | GTG | AAG | AAC | 1507 |
| Pro | Ile | Val | His | Arg | Asp | Leu | Lys | Ser | Ser | Asn | Ile | Leu | Val | Lys | Asn |      |
|     | 375 |     |     |     | 380 |     |     |     |     |     | 385 |     |     |     |     |      |
| GAC | CTA | ACC | TGC | TGC | CTG | TGT | GAC | TTT | GGG | CTT | TCC | CTG | CGT | CTG | GAC | 1555 |
| Asp | Leu | Thr | Cys | Cys | Leu | Cys | Asp | Phe | Gly | Leu | Ser | Leu | Arg | Leu | Asp |      |
| 390 |     |     |     |     | 395 |     |     |     | 400 |     |     |     |     | 405 |     |      |
| CCT | ACT | CTG | TCT | GTG | GAT | GAC | CTG | GCT | AAC | AGT | GGG | CAG | GTG | GGA | ACT | 1603 |
| Pro | Thr | Leu | Ser | Val | Asp | Asp | Leu | Ala | Asn | Ser | Gly | Gln | Val | Gly | Thr |      |
|     |     |     |     | 410 |     |     |     |     | 415 |     |     |     | 420 |     |     |      |
| GCA | AGA | TAC | ATG | GCT | CCA | GAA | GTC | CTA | GAA | TCC | AGG | ATG | AAT | TTG | GAG | 1651 |
| Ala | Arg | Tyr | Met | Ala | Pro | Glu | Val | Leu | Glu | Ser | Arg | Met | Asn | Leu | Glu |      |
|     |     |     | 425 |     |     |     |     | 430 |     |     |     |     | 435 |     |     |      |
| AAT | GCT | GAG | TCC | TTC | AAG | CAG | ACC | GAT | GTC | TAC | TCC | ATG | GCT | CTG | GTG | 1699 |
| Asn | Ala | Glu | Ser | Phe | Lys | Gln | Thr | Asp | Val | Tyr | Ser | Met | Ala | Leu | Val |      |
|     |     | 440 |     |     |     |     | 445 |     |     |     |     | 450 |     |     |     |      |
| CTC | TGG | GAA | ATG | ACA | TCT | CGC | TGT | AAT | GCA | GTG | GGA | GAA | GTA | AAA | GAT | 1747 |
| Leu | Trp | Glu | Met | Thr | Ser | Arg | Cys | Asn | Ala | Val | Gly | Glu | Val | Lys | Asp |      |
|     | 455 |     |     |     |     | 460 |     |     |     | 465 |     |     |     |     |     |      |
| TAT | GAG | CCT | CCA | TTT | GGT | TCC | AAG | GTG | CGG | GAG | CAC | CCC | TGT | GTC | GAA | 1795 |
| Tyr | Glu | Pro | Pro | Phe | Gly | Ser | Lys | Val | Arg | Glu | His | Pro | Cys | Val | Glu |      |
| 470 |     |     |     |     | 475 |     |     |     | 480 |     |     |     |     | 485 |     |      |
| AGC | ATG | AAG | GAC | AAC | GTG | TTG | AGA | GAT | CGA | GGG | CGA | CCA | GAA | ATT | CCC | 1843 |
| Ser | Met | Lys | Asp | Asn | Val | Leu | Arg | Asp | Arg | Gly | Arg | Pro | Glu | Ile | Pro |      |
|     |     |     |     | 490 |     |     |     | 495 |     |     |     |     | 500 |     |     |      |
| AGC | TTC | TGG | CTC | AAC | CAC | CAG | GGC | ATC | CAG | ATG | GTG | TGT | GAG | ACG | TTG | 1891 |
| Ser | Phe | Trp | Leu | Asn | His | Gln | Gly | Ile | Gln | Met | Val | Cys | Glu | Thr | Leu |      |
|     |     |     | 505 |     |     |     | 510 |     |     |     |     | 515 |     |     |     |      |
| ACT | GAG | TGC | TGG | GAC | CAC | GAC | CCA | GAG | GCC | CGT | CTC | ACA | GCC | CAG | TGT | 1939 |
| Thr | Glu | Cys | Trp | Asp | His | Asp | Pro | Glu | Ala | Arg | Leu | Thr | Ala | Gln | Cys |      |
|     |     | 520 |     |     |     |     | 525 |     |     |     | 530 |     |     |     |     |      |
| GTG | GCA | GAA | CGC | TTC | AGT | GAG | CTG | GAG | CAT | CTG | GAC | AGG | CTC | TCG | GGG | 1987 |
| Val | Ala | Glu | Arg | Phe | Ser | Glu | Leu | Glu | His | Leu | Asp | Arg | Leu | Ser | Gly |      |
|     | 535 |     |     |     |     | 540 |     |     |     |     | 545 |     |     |     |     |      |
| AGG | AGC | TGC | TCG | GAG | GAG | AAG | ATT | CCT | GAA | GAC | GGC | TCC | CTA | AAC | ACT | 2035 |
| Arg | Ser | Cys | Ser | Glu | Glu | Lys | Ile | Pro | Glu | Asp | Gly | Ser | Leu | Asn | Thr |      |

|  | 550 | 555 | 560 | 565 |  |
|---|---|---|---|---|---|
| ACC | AAA | TAGCTCTTAT GGGGCAGGCT GGGCATGTCC AAAGAGGCTG CCCCTCTCAC | | | 2091 |
| Thr | Lys | | | | |
| CAAA | | | | | 2095 |

( 2 ) INFORMATION FOR SEQ ID NO:2:

( i ) SEQUENCE CHARACTERISTICS:
  ( A ) LENGTH: 567 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

```
Met Gly Arg Gly Leu Leu Arg Gly Leu Trp Pro Leu His Ile Val Leu
 1               5                  10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285

Thr Glu Lys Asp Ile Phe Ser Asp Ile Asn Leu Lys His Glu Asn Ile
    290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
```

|  |  |  |  | 325 |  |  |  | 330 |  |  |  | 335 |  |  |
|--|--|--|--|--|--|--|--|--|--|--|--|--|--|--|
| Leu | Thr | Arg | His 340 | Val | Ile | Ser | Trp | Glu 345 | Asp | Leu | Arg | Lys | Leu 350 | Gly | Ser |
| Ser | Leu | Ala 355 | Arg | Gly | Ile | Ala | His 360 | Leu | His | Ser | Asp | His 365 | Thr | Pro | Cys |
| Gly | Arg 370 | Pro | Lys | Met | Pro 375 | Ile | Val | His | Arg | Asp | Leu 380 | Lys | Ser | Ser | Asn |
| Ile 385 | Leu | Val | Lys | Asn 390 | Asp | Leu | Thr | Cys | Cys 395 | Leu | Cys | Asp | Phe | Gly | Leu 400 |
| Ser | Leu | Arg | Leu | Asp 405 | Pro | Thr | Leu | Ser | Val 410 | Asp | Asp | Leu | Ala | Asn 415 | Ser |
| Gly | Gln | Val | Gly 420 | Thr | Ala | Arg | Tyr | Met 425 | Ala | Pro | Glu | Val | Leu 430 | Glu | Ser |
| Arg | Met | Asn 435 | Leu | Glu | Asn | Ala | Glu 440 | Ser | Phe | Lys | Gln | Thr 445 | Asp | Val | Tyr |
| Ser | Met 450 | Ala | Leu | Val | Leu | Trp 455 | Glu | Met | Thr | Ser | Arg 460 | Cys | Asn | Ala | Val |
| Gly 465 | Glu | Val | Lys | Asp | Tyr 470 | Glu | Pro | Pro | Phe | Gly 475 | Ser | Lys | Val | Arg | Glu 480 |
| His | Pro | Cys | Val | Glu 485 | Ser | Met | Lys | Asp | Asn 490 | Val | Leu | Arg | Asp | Arg 495 | Gly |
| Arg | Pro | Glu | Ile 500 | Pro | Ser | Phe | Trp | Leu 505 | Asn | His | Gln | Gly | Ile 510 | Gln | Met |
| Val | Cys | Glu 515 | Thr | Leu | Thr | Glu | Cys 520 | Trp | Asp | His | Asp | Pro 525 | Glu | Ala | Arg |
| Leu | Thr 530 | Ala | Gln | Cys | Val | Ala 535 | Glu | Arg | Phe | Ser | Glu 540 | Leu | Glu | His | Leu |
| Asp 545 | Arg | Leu | Ser | Gly | Arg 550 | Ser | Cys | Ser | Glu | Glu 555 | Lys | Ile | Pro | Glu | Asp 560 |
| Gly | Ser | Leu | Asn | Thr 565 | Thr | Lys |  |  |  |  |  |  |  |  |  |

(2) INFORMATION FOR SEQ ID NO:3:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:3:

```
GGATCCCGTG GAGGATTAAA CCATGGATGG ATGCATAAGC TTCGAATTC                    49
```

(2) INFORMATION FOR SEQ ID NO:4:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO:4:

```
GGGGATCCGA TAGTGGAGGA TGATTAAATG ATCCCACCGC ACGTTCAGAA GT                52
```

(2) INFORMATION FOR SEQ ID NO:5:

(i) SEQUENCE CHARACTERISTICS:
        (A) LENGTH: 46 base pairs
        (B) TYPE: nucleic acid
        (C) STRANDEDNESS: single (D) TOPOLOGY: linear (x i) SEQUENCE DESCRIPTION: SEQ ID NO:5:

GGGGAATTCA AGCTTAGTCA GGATTGCTGG TGTTATATTC TTCTGA    46

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (x i) SEQUENCE DESCRIPTION: SEQ ID NO:6:

GGGGCCGCGG TGGTATCCCA CCGCACGTTC AGAAGTCGGT T    41

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (x i) SEQUENCE DESCRIPTION: SEQ ID NO:7:

TAGCAACAAG TCAGGTTAGC TGGTGTTATA TTC    33